(12) United States Patent
Pedroni

(10) Patent No.: US 10,688,287 B2
(45) Date of Patent: Jun. 23, 2020

(54) SHEATH INCLUDING SHEATH BODY AND SHEATH INSERT

(71) Applicant: Medtronic, Inc., Minneapolis, MN (US)

(72) Inventor: Chiara Pedroni, Milan (IT)

(73) Assignee: Medtronic, Inc., Minneapolis, MN (US)

( * ) Notice: Subject to any disclaimer, the term of this patent is extended or adjusted under 35 U.S.C. 154(b) by 255 days.

(21) Appl. No.: 15/875,331

(22) Filed: Jan. 19, 2018

(65) Prior Publication Data

US 2019/0224459 A1 Jul. 25, 2019

(51) Int. Cl.
| | | |
|---|---|---|
| *A61M 31/00* | (2006.01) | |
| *A61M 37/00* | (2006.01) | |
| *A61M 25/10* | (2013.01) | |
| *A61M 25/06* | (2006.01) | |

(52) U.S. Cl.
CPC ........ *A61M 25/10* (2013.01); *A61M 25/0668* (2013.01); *A61M 2025/0675* (2013.01); *A61M 2025/105* (2013.01); *A61M 2025/1081* (2013.01)

(58) Field of Classification Search
CPC .... A61M 2025/0675; A61M 2025/105; A61M 2025/1081; A61M 25/0668; A61M 25/10
See application file for complete search history.

(56) References Cited

U.S. PATENT DOCUMENTS

| | | |
|---|---|---|
| 5,188,605 A | 2/1993 | Sleep |
| 5,647,857 A | 7/1997 | Anderson et al. |
| 5,868,719 A | 2/1999 | Tsukernik |
| 5,964,730 A | 10/1999 | Williams et al. |
| 6,110,146 A | 8/2000 | Berthiaume et al. |
| 6,592,548 B2 | 7/2003 | Jayaraman |
| 7,105,013 B2 | 9/2006 | Durcan |
| 8,414,528 B2 | 4/2013 | Liu et al. |
| 8,852,257 B2 | 10/2014 | Liu et al. |
| 9,072,590 B2 | 7/2015 | Wang et al. |
| 9,119,741 B2 | 9/2015 | Liu et al. |
| 2009/0105686 A1* | 4/2009 | Snow ...................... A61F 2/958 604/509 |
| 2011/0270226 A1 | 11/2011 | Kocur et al. |

(Continued)

OTHER PUBLICATIONS

U.S. Appl. No. 15/875,356, filed Jan. 19, 2018, naming inventors Connors et al.

(Continued)

*Primary Examiner* — Rebecca E Eisenberg
(74) *Attorney, Agent, or Firm* — Shumaker & Sieffert P.A.

(57) ABSTRACT

In some examples, a device includes a catheter and a sheath. The catheter includes a catheter body and an expandable balloon positioned on the catheter body. The sheath includes a sheath body including a wall defining a lumen configured to receive the expandable balloon, the wall defining a channel extending longitudinally at least partially between a proximal end of the sheath body and a distal end of the sheath body, and a sheath insert configured to close the channel. The sheath insert includes a septum configured to be removably received within the channel, and a flange extending from the septum and configured to retain the septum within the channel when the septum is received within the channel.

25 Claims, 13 Drawing Sheets

(56) References Cited

U.S. PATENT DOCUMENTS

| | | | |
|---|---|---|---|
| 2012/0296313 A1* | 11/2012 | Andreacchi | A61M 25/0668 |
| | | | 604/509 |
| 2013/0018309 A1 | 1/2013 | Ewing et al. | |
| 2014/0379065 A1 | 12/2014 | Johnson et al. | |
| 2015/0088241 A1 | 3/2015 | Liu et al. | |
| 2015/0224282 A1* | 8/2015 | Christiansen | A61M 25/0668 |
| | | | 604/164.01 |
| 2015/0328028 A1 | 11/2015 | Wang et al. | |
| 2016/0058983 A1 | 3/2016 | Poker et al. | |
| 2018/0043138 A1 | 2/2018 | Chu | |

OTHER PUBLICATIONS

U.S. Appl. No. 15/875,343, filed Jan. 19, 2018, naming inventors Traxler et al.
U.S. Appl. No. 15/875,372, filed Jan. 19, 2018, naming inventors Kantor et al.
U.S. Appl. No. 15/875,318, filed Jan. 19, 2018, naming inventors Massimo et al.

* cited by examiner

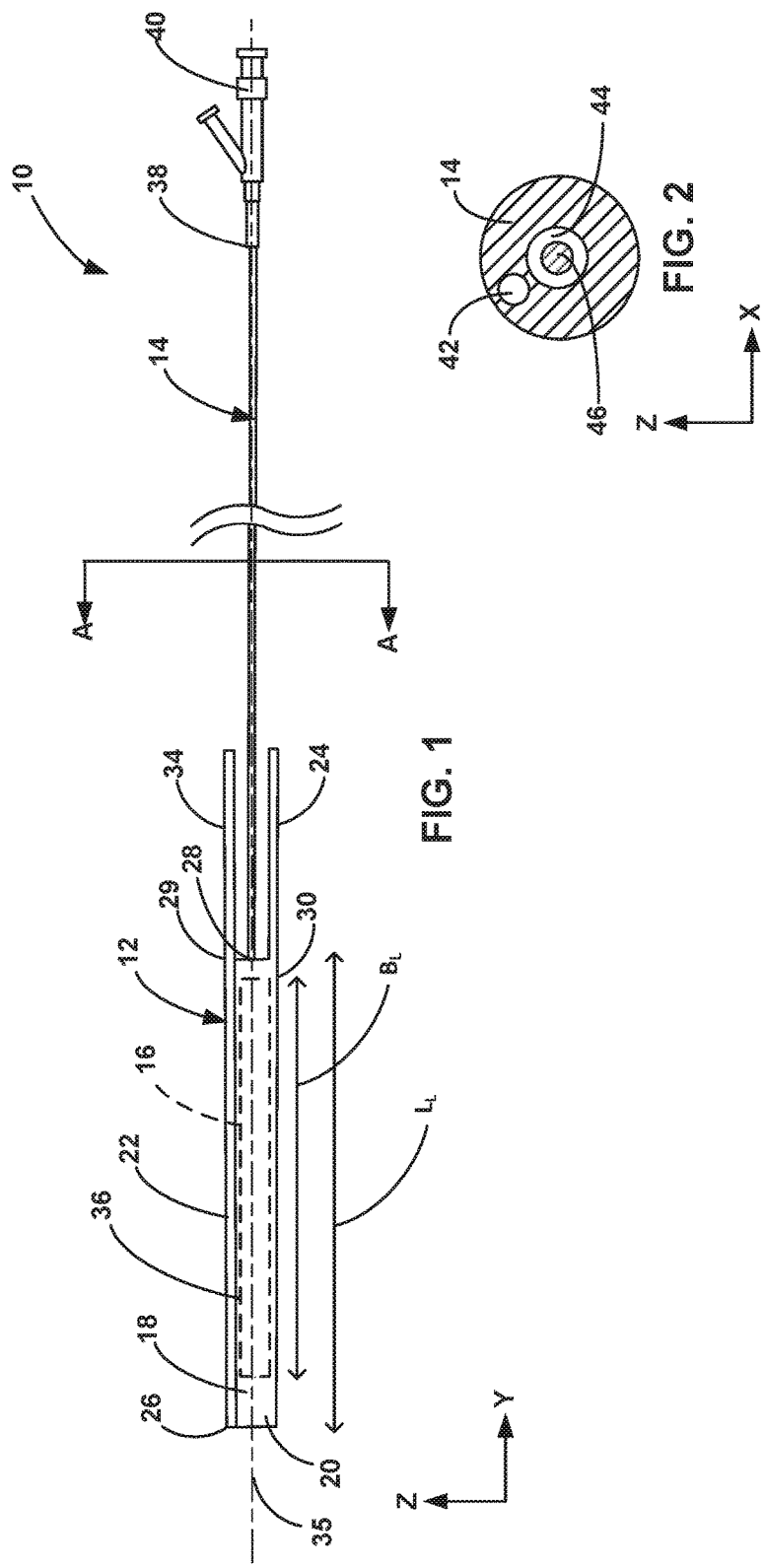
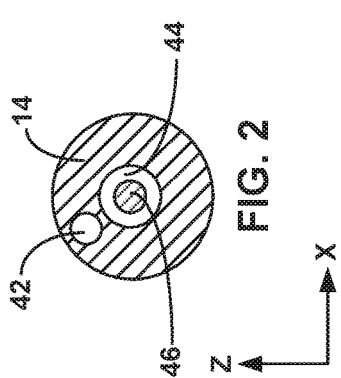
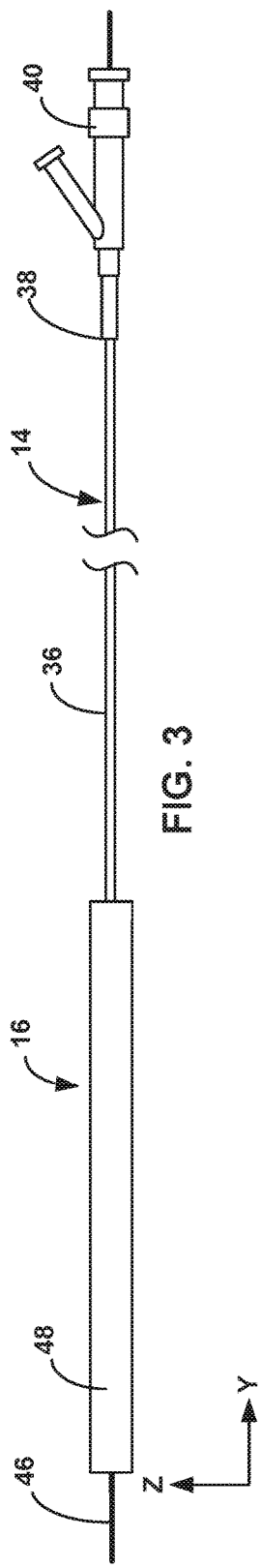

US 10,688,287 B2

SHEATH INCLUDING SHEATH BODY AND SHEATH INSERT

TECHNICAL FIELD

The disclosure relates generally to sheaths for medical devices, and more specifically to splittable sheaths, and to methods of using sheaths, and medical devices assemblies including the sheaths.

BACKGROUND

Portions of the vasculature of a patient may be treated to restore adequate blood flow in an occluded blood vessel. Conditions for which blood-flow restoration may be indicated include atherosclerosis and other conditions that may cause narrowing of a lumen of a blood vessel. In some examples, a system for restoring adequate blood flow may include an expandable balloon positioned on a catheter and received within a sheath. During treatment, a clinician may advance the balloon through the sheath and into the vasculature of the patient, navigate the balloon to a treatment site within a target vessel, and then expand the balloon to restore patency of the target vessel. Some balloon sheaths may be configured to be longitudinally split into two portions to enable a clinician to remove the sheath from the catheter once the balloon has been advanced through the sheath. In some examples, expandable balloons may include a drug coating to help prevent re-stenosis of the target vessel.

SUMMARY

This disclosure describes example splittable sheaths that can be used, for example, to protect an expandable balloon prior to the introduction of the balloon into the vasculature of a patient. The disclosure also describes example devices that include a splittable sheath defining a lumen, and an expandable balloon positioned on a catheter and configured to be received within the lumen of the splittable sheath. Also described herein are methods of using devices that comprise the balloon catheter and the splittable sheath.

Example splittable sheaths described herein include a sheath body defining a longitudinally extending channel and a sheath insert configured to be received within the channel of the sheath body. Movement of the sheath insert in a direction away from the sheath body causes the sheath insert and the sheath body to separate from each other, thereby splitting the splittable sheath and enabling the sheath to be removed from around a catheter. The channel defines a predetermined path along which the splittable sheath may split in a predictable manner when a clinician moves the sheath body and/or the sheath insert to split the splittable sheath. In some examples, the sheath insert includes a septum configured to be received within the channel of the sheath body, and one or more flanges extending from the septum and configured to retain the septum within the channel.

In a first example, aspects of the disclosure relate to a device that includes: a catheter comprising: a catheter body; and an expandable balloon positioned on the catheter body; and a sheath including: a sheath body including a wall defining a lumen configured to receive the expandable balloon, the wall defining a channel extending longitudinally at least partially between a proximal end of the sheath body and a distal end of the sheath body; and a sheath insert configured to close the channel, the sheath insert including: a septum configured to be removably received within the channel; and a flange extending from the septum and configured to retain the septum within the channel when the septum is received within the channel.

In a second example, aspects of the disclosure relate to a device that includes: a sheath body including a wall defining a lumen configured to receive an expandable balloon of a catheter, the wall defining a channel extending longitudinally at least partially between a proximal end of the sheath body and a distal end of the sheath body; and a sheath insert configured to close the channel, the sheath insert including: a septum configured to be removably received within the channel; and a flange configured to retain the septum within the channel when the septum is received within the channel.

In a third example relating to the devices of the first or second examples, the sheath insert is configured to extend at least partially between the proximal end of the sheath body and the distal end of the sheath body when the septum is received within the channel.

In a fourth example relating to the device of the third example, the sheath insert is configured to extend from the proximal end of the sheath body to the distal end of the sheath body when the septum is received within the channel.

In a fifth example relating to the device of any of the first through fourth examples, the flange is integrally formed with the septum.

In a sixth example relating to the device of any of the first through fifth examples, the sheath insert and the sheath body are movable relative to each other in only a longitudinal direction when the septum is received within the channel.

In a seventh example relating to the device of any of the first through sixth examples, the sheath insert is configured to retain the sheath body in a substantially tubular shape.

In an eighth example relating to the device of any of the first through seventh examples, the flange is an outer flange and the sheath insert further includes an inner flange extending from the septum and configured to be received within the lumen of the sheath body when the septum is received within the channel.

In a ninth example relating to the device of the eighth example, the sheath body defines an inner surface facing the lumen and an outer surface, and wherein the outer flange is configured to contact the outer surface of the wall of the sheath body when the septum is received within the channel, and the inner flange is configured to contact the inner surface of the wall of the sheath body when the septum is received within the channel.

In a tenth example relating to the device of the eighth example or the ninth example, the inner flange is integrally formed with the septum.

In an eleventh example relating to the device of any of the first through tenth examples, a shape of a cross-section of the sheath insert taken orthogonal to a longitudinal axis of the sheath insert is one of an I-shape or a T-shape.

In a twelfth example relating to the device of any of the first through eleventh examples, the sheath body defines an inner surface facing the lumen and an outer surface, and wherein, when the expandable balloon is received within the lumen of the sheath body and the septum is received within the channel, the expandable balloon is configured to exert a radially-outward force on the inner surface of the wall of the sheath body.

In a thirteenth example relating to the example of the device of any of the first through twelfth examples, the flange is configured to extend along an outer surface of the wall of the sheath body when the septum is received within the channel.

In a fourteenth example relating to the device of any of the first through eighth examples or any of the tenth through twelfth examples, the wall of the sheath body defines a recess, and the flange is configured to be received within the recess when the septum is received within the channel.

In a fifteenth example relating to the device of the fourteenth example, a thickness of the flange is substantially equal to a depth of the recess such that an outer surface of the flange is flush with the outer surface of the wall of the sheath body when the septum is received within the channel.

In a sixteenth example relating to the device of any of the first through fifteenth examples, the wall of the sheath body defines: a first edge extending longitudinally at least partially between the proximal end of the sheath body and the distal end of the sheath body; and a second edge extending longitudinally at least partially between the proximal end of the sheath body and the distal end of the sheath body, wherein the first edge and the second edge are separated by the channel.

In a seventeenth example relating to the device of the sixteenth example, the first edge of the sheath body is configured to contact a first surface of the septum and the second edge of the sheath body is configured to contact a second surface of the septum when the septum is received within the channel, and wherein the first surface and the second surface of the septum extend longitudinally along opposite sides of the septum.

In an eighteenth example relating to the device of the seventeenth example, at least one of the first surface of the septum or the second surface of the septum includes a lubricious coating.

In a nineteenth example relating to the device of the seventeenth example or the eighteenth example, the septum is configured to be held within the channel by a mechanical interference fit.

In a twentieth example relating to the device of any of the sixteenth through nineteenth examples, a first distance between the first edge and the second edge at a proximal portion of the sheath body is different from a second distance between the first edge and the second edge at a distal portion of the sheath body.

In a twenty-first example relating to the device of the twentieth example, the septum has a first width of about 0.40 millimeters to about 1.00 millimeters at a proximal end of the septum and a second width of about 0.30 millimeters to about 0.75 millimeters at a distal end of the septum, the second width being different from the first width, the first width and the second width being measured in a direction orthogonal to a longitudinal axis of the sheath insert.

In a twenty-second example relating to the device of any of the sixteenth through nineteenth examples, a distance between the first and second edges is substantially constant along a length of the first edge, the distance being measured in a direction orthogonal to a longitudinal axis of the sheath insert.

In a twenty-third example relating to the device of the twenty-second example, the septum has a width of about 0.30 millimeters to about 1.00 millimeters, the width being measured in a direction orthogonal to a longitudinal axis of the sheath insert.

In a twenty-fourth example relating to the device of any of the sixteenth through twenty-third examples, less than an entirety of the first edge of the sheath body is configured to contact the first surface of the septum, and wherein less than an entirety of the second edge of the sheath body is configured to contact the second surface of the septum when the septum is received within the channel.

In a twenty-fifth example relating to the device of any of the first through twenty-fourth examples, an inner diameter of the lumen of the sheath body is about 1.35 millimeters to about 2.00 millimeters.

In a twenty-sixth example relating to the device of any of the first through twenty-fifth examples, the sheath insert includes a tab extending from one of a proximal end or a distal end of the sheath insert, the tab defining a user gripping surface.

In a twenty-seventh example relating to the device of the twenty-sixth example, the tab is attached to the sheath insert by at least one of overmolding, bonding, welding, or an adhesive.

In a twenty-eighth example relating to the device of the twenty-sixth example, the tab of the sheath insert is integrally formed with the sheath insert.

In a twenty-ninth example relating to the device of any of the twenty-sixth through the twenty-eighth examples, when the septum is received within the channel, the sheath insert and the sheath body are configured to be separated from each other in response to a pulling force applied to the tab of the sheath insert in a direction away from the sheath body.

In a thirtieth example relating to the device of any of the twenty-sixth through the twenty-ninth examples, the tab comprises a first tab, the sheath body including a second tab extending from the one of the proximal end or the distal end of the sheath insert.

In a thirty-first example relating to the device of the thirtieth example, the sheath insert and the sheath body are configured to be separated from each other in response to movement of at least one of the first tab of the sheath insert or the second tab of the sheath body in a direction away from a central longitudinal axis of the sheath.

In a thirty-second example relating to the device of any of the first through the thirty-first examples, the sheath body comprises at least one of polytetrafluoroethylene (PTFE), high-density polyethylene (HDPE) or low-density polyethylene (LDPE).

In a thirty-third example relating to the device of any of the first through thirty-second examples, the wall of the sheath body defines an inner surface facing the lumen and the device further includes a pharmacologically-active agent on an outer surface of the balloon, wherein a material of the inner surface of the wall is substantially chemically non-reactive with the pharmacologically-active agent.

In a thirty-fourth example relating to the device of the thirty-third example, the pharmacologically-active agent includes at least one of an antiproliferative agent or an anti-restenotic agent.

In a thirty-fifth example, aspects of the disclosure relate to a method that includes: separating a sheath from a catheter, wherein separating the sheath from the catheter includes separating a sheath body of the sheath and a sheath insert of the sheath, the sheath being disposed around an expandable balloon of the catheter, the sheath including: a sheath body including a wall defining a lumen configured to receive the expandable balloon, the wall defining an inner surface facing the lumen, an outer surface, and a channel between the inner surface and the outer surface that extends longitudinally at least partially between a proximal end of the sheath body and a distal end of the sheath body; and the sheath insert, the sheath insert including: a septum configured to be removably received within the channel; and a flange configured to retain the septum within the channel when the septum is received within the channel.

In a thirty-sixth example relating to the method of the thirty-fifth example, separating the sheath body and the sheath insert includes moving a first tab of the sheath insert and a second tab of the sheath body outward relative to a central longitudinal axis of the sheath.

In a thirty-seventh example relating to the method of the thirty-sixth example, separating the sheath body and the sheath insert includes applying a pulling force to a tab of the sheath insert in a direction away from the sheath body.

In a thirty-eighth example relating to the method of any of the thirty-fifth through thirty-seventh examples, the method further includes, before separating the sheath body and the sheath insert, advancing the expandable balloon distally through the lumen of the sheath body and into a lumen of an introducer.

In a thirty-ninth example relating to the method of any of the thirty-fifth through thirty-eighth examples, the method further includes advancing the catheter to a treatment site within a vasculature of a patient and inflating the expandable balloon.

In a fortieth example relating to the method of any of the thirty-fifth through thirty-ninth examples, the sheath insert is configured to extend at least partially between the proximal end of the sheath body and the distal end of the sheath body when the septum is received within the channel.

In a forty-first example relating to the method of thirty-fifth through fortieth examples, the sheath insert is configured to extend from the proximal end of the sheath body to the distal end of the sheath body when the septum is received within the channel.

In a forty-second example relating to the method of any of the thirty-fifth through forty-first examples, the flange is integrally formed with the septum.

In a forty-third example relating to the method of any of the thirty-fifth through forty-second examples, the sheath insert and the sheath body are movable relative to each other in only a longitudinal direction when the septum is received within the channel.

In a forty-fourth example relating to the method of the method of any of the thirty-fifth through forty-third examples, the sheath insert is configured to retain the sheath body in a substantially tubular shape.

In a forty-fifth example relating to the method of any of the thirty-fifth through forty-fourth examples, the flange is an outer flange and the sheath insert further includes an inner flange extending from the septum and configured to be received within the lumen of the sheath body when the septum is received within the channel.

In a forty-sixth example relating to the method of the forty-fifth example, the sheath body defines an inner surface facing the lumen and an outer surface, and wherein the outer flange is configured to contact the outer surface of the wall of the sheath body when the septum is received within the channel, and the inner flange is configured to contact the inner surface of the sheath body when the septum is received within the channel.

In a forty-seventh example relating to the method of the forty-fifth example or the forty-sixth example, the inner flange is integrally formed with the septum.

In a forty-eighth example relating to the method of any of the thirty-fifth through forty-seventh examples, a shape of a cross-section of the sheath insert taken orthogonal to a longitudinal axis of the sheath insert is one of an I-shape or a T-shape.

In a forty-ninth example relating to the method of any of the thirty-fifth through forty-eighth examples, the sheath body defines an inner surface facing the lumen and an outer surface, and wherein, when the expandable balloon is received within the lumen of the sheath body and the septum is received within the channel, the expandable balloon is configured to exert a radially-outward force on the inner surface of the sheath body.

In a fiftieth example relating to the example of the method of any of the thirty-fifth through forty-ninth examples, the flange is configured to extend along an outer surface of the wall of the sheath body when the septum is received within the channel.

In a fifty-first example relating to the method of any of the thirty-fifth through forty-fifth examples or any of the forty-seventh through fiftieth examples, the wall of the sheath body defines a recess, and the flange is configured to be received within the recess when the septum is received within the channel.

In a fifty-second example relating to the method of the fifty-first example, a thickness of the flange is substantially equal to a depth of the recess such that an outer surface of the flange is flush with the outer surface of the wall of the sheath body when the septum is received within the channel.

In a fifty-third example relating to the method of any of the thirty-fifth through fifty-second examples, the wall of the sheath body defines: a first edge extending longitudinally at least partially between the proximal end of the sheath body and the distal end of the sheath body; and a second edge extending longitudinally at least partially between the proximal end of the sheath body and the distal end of the sheath body, wherein the first edge and the second edge are separated by the channel.

In a fifty-fourth example relating to the method of the fifty-third example, the first edge of the sheath body is configured to contact a first surface of the septum and the second edge of the sheath body is configured to contact a second surface of the septum when the septum is received within the channel, and wherein the first surface and the second surface of the septum extend longitudinally along opposite sides of the septum.

In a fifty-fifth example relating to the method of the fifty-fourth example, at least one of the first surface of the septum or the second surface of the septum includes a lubricious coating.

In a fifty-sixth example relating to the method of the fifty-fourth example or the fifty-fifth example, the septum is configured to be held within the channel by a mechanical interference fit.

In a fifty-seventh example relating to the method of any of the fifty-third through fifty-sixth examples, a first distance between the first edge and the second edge at a proximal portion of the sheath body is different from a second distance between the first edge and the second edge at a distal portion of the sheath body.

In a fifty-eighth example relating to the method of the fifty-seventh example, the septum has a first width of about 0.40 millimeters to about 1.00 millimeters at a proximal end of the septum and a second width of about 0.30 millimeters to about 0.75 millimeters at a distal end of the septum that is different from the first width, the first width and the second width being measured in a direction orthogonal to a longitudinal axis of the sheath insert.

In a fifty-ninth example relating to the method of any of the fifty-third through fifty-sixth examples, a distance between the first and second edges is substantially constant along a length of the first edge, the distance being measured in a direction orthogonal to a longitudinal axis of the sheath insert.

In a sixtieth example relating to the method of the fifty-ninth example, the septum has a width of about 0.30 millimeters to about 1.00 millimeters, the width being measured in a direction orthogonal to a longitudinal axis of the sheath insert.

In a sixty-first example relating to the method of any of the fifty-third through sixtieth examples, less than an entirety of the first edge of the sheath body is configured to contact the first surface of the septum, and wherein less than an entirety of the second edge of the sheath body is configured to contact the second surface of the septum when the septum is received within the channel.

In a sixty-second example relating to the method of any of the thirty-fifth through sixty-first examples, an inner diameter of the lumen of the sheath body is about 1.35 millimeters to about 2.00 millimeters.

In a sixty-third example relating to the method of any of the thirty-fifth through sixty-second examples, the sheath insert includes a tab extending from one of a proximal end or a distal end of the sheath insert, the tab defining a user gripping surface.

In a sixty-fourth example relating to the method of the sixty-third example, the tab is attached to the sheath insert by at least one of overmolding, bonding, welding, or an adhesive.

In a sixty-fifth example relating to the method of the sixty-third example, the tab of the sheath insert is integrally formed with the sheath insert.

In a sixty-sixth example relating to the method of any of the sixty-third through sixty-fifth examples, when the septum is received within the channel, the sheath insert and the sheath body are configured to be separated from each other in response to a pulling force applied to the tab of the sheath insert in a direction away from the sheath body.

In a sixty-seventh example relating to the method of any of the sixty-third through sixty-sixth examples, the tab comprises a first tab, the sheath body including a second tab extending from the one of the proximal end or the distal end of the sheath insert.

In a sixty-eighth example relating to the method of the sixty-seventh example, the sheath insert and the sheath body are configured to be separated from each other in response to movement of at least one of the first tab of the sheath insert or the second tab of the sheath body in a direction away from a central longitudinal axis of the sheath.

In a sixty-ninth example relating to the method of any of the thirty-fifth through sixty-eighth examples, the sheath body includes at least one of polytetrafluoroethylene (PTFE), high-density polyethylene (HDPE) or low-density polyethylene (LDPE).

In a seventieth example relating to the method of any of the thirty-fifth through sixty-ninth examples, the catheter includes a pharmacologically-active agent on an outer surface of the balloon and the sheath body defines an inner surface facing the lumen, wherein a material of the inner surface of the sheath body is substantially chemically non-reactive with the pharmacologically-active agent.

In a seventy-first example relating to the method of the seventieth example, the pharmacologically-active agent includes at least one of an antiproliferative agent or an anti-restenotic agent.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 1 is a side view of an example device comprising a splittable sheath and catheter including an expandable balloon positioned on a catheter body and received within a lumen of the splittable sheath.

FIG. 2 is a cross-sectional view of the catheter of FIG. 1, where the cross-section is taken along a plane A-A orthogonal to a longitudinal axis of the catheter.

FIG. 3 is a side view of the catheter of FIG. 1, where the expandable balloon is positioned on the catheter body in a collapsed configuration.

Figure 4A:
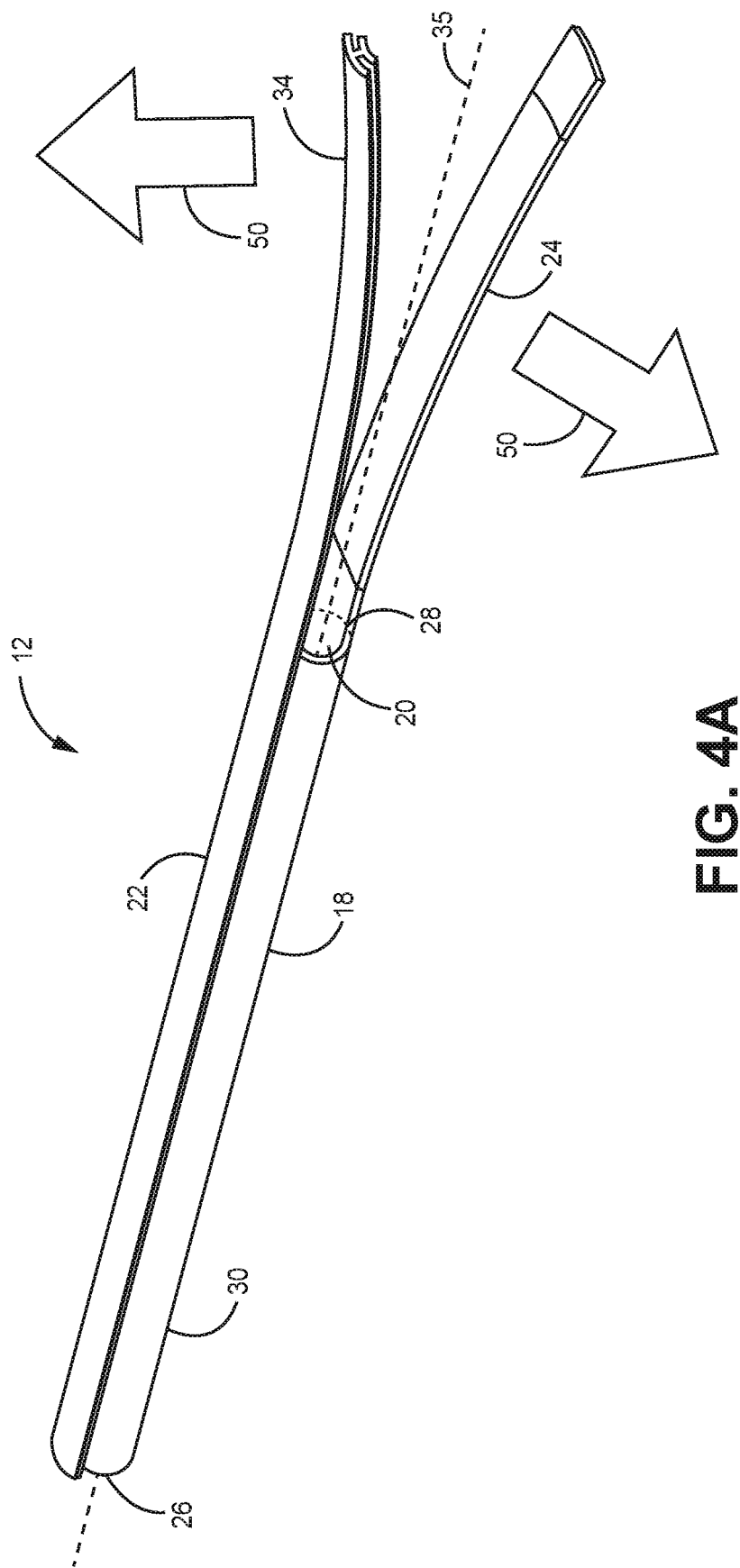
FIG. 4A is a perspective view of the splittable sheath of FIG. 1 in an assembled configuration.

The details of one or more examples of this disclosure are set forth in the accompanying drawings and the description below. Other features, objects, and advantages of this disclosure will be apparent from the description and drawings, and from the claims.

DETAILED DESCRIPTION

Conditions related to the narrowing of blood vessels within the human body affect millions of people worldwide. In some cases, narrowing of a blood vessel can be caused by a buildup of plaque within the lumen of the vessel or within the vessel wall (atherosclerosis). Atherosclerosis may occur in portions of the vasculature that supply the heart, brain, and other regions of the body including the limbs. If not treated, the reduction in blood flow caused by atherosclerosis can lead to heart attack, stroke, tissue death in the extremities, and other adverse outcomes. Options for restoring adequate blood flow in a vessel affected by atherosclerosis include angioplasty procedures, which may include the delivery of expandable balloons, stents and/or drugs to the vessel.

In some examples, angioplasty procedures for restoring blood flow to an affected vessel may include inflating an expandable balloon within the affected vessel to compress accumulated plaque against the vessel wall. For example, a clinician may introduce a catheter having an expandable balloon into the vasculature of a patient via an introducer sheath placed in a small incision in the patient's skin. The clinician then may advance the catheter to a treatment site in the target vessel, and inflate the expandable balloon via an inflation lumen within the catheter. In some examples, an expandable balloon may be coated with or otherwise carry a pharmacologically-active agent, such as an anticoagulant, anti-inflammatory agent, antiproliferative, or other drug. This may be referred to as a drug-coated balloon. The pharmacologically-active agent may be transferred from an outer surface of the expandable balloon to the tissue of the target vessel when the expandable balloon is inflated and contacts the tissue. In this manner, drug-coated balloons may provide added clinical benefit to angioplasty procedures by delivering pharmacologically-active agents directly to the affected vessel, and thereby reducing the likelihood of vessel re-stenosis.

In some cases, it may be beneficial to protect a balloon of a catheter following manufacture and prior to introduction into a body of a patient. For example, the balloon may be subject to kinking, stretching, scratches, cuts, or self-adhesion of balloon components during packaging, shipping, storage, or handling. With some drug-coated balloons, a drug coating on an outer surface of the balloon may be eroded after manufacture and prior to use of the balloon during the packaging, shipping, storage, or handling of the balloon prior to being introduced. A protective sheath positioned at least partially over the balloon may help maintain the structural integrity of the balloon, the integrity of the drug coating, or the structural integrity of both the balloon and the drug coating. In examples in which the balloon is folded in order to maintain a low profile for introduction into a patient, the protective sheath may also maintain the balloon in the folded state and resulting low-profile configuration.

In some examples, a protective balloon sheath may be applied at least partially over the balloon following manufacture and assembly of the balloon catheter, but prior to packaging of the balloon catheter. Such balloon sheaths may help protect the structural integrity of the balloon and any drug coatings thereon by shielding the balloon from direct physical contact with the external environment prior to introduction of the balloon into a patient's body. For example, the balloon sheath may enable a clinician to avoid handling the balloon directly. Instead, the clinician may attach the balloon sheath to an introducer sheath, and advance the balloon through the balloon sheath, through the introducer sheath, and into the vasculature of the patient by manipulating a catheter body of the balloon catheter.

A balloon sheath may be a tubular structure that is configured to be positioned around a catheter body. In example medical devices having a balloon sheath that is not configured to be easily removable from over a catheter, a portion of the catheter equal to a length of a body of the sheath may be operationally unusable, as the sheath may not be slidable proximally over a manifold or other hub at a proximal end of the catheter or distally into an introducer sheath used to aid introduction of the balloon catheter into vasculature of a patient. In such example medical devices, a length of a catheter may need to be increased to account for an operationally unusable length of the catheter, thereby increasing the amount of material needed to manufacture the catheter and increasing the overall length of the catheter. Removing a balloon sheath from around a catheter may enable substantially an entire length of a catheter body to be operationally usable, including a length of the catheter body housed within the balloon sheath when an expandable balloon is received within a lumen of the balloon sheath. While a clinician may cut the balloon sheath off the catheter, cutting the balloon sheath off the catheter may require an additional cutting tool, as well as additional time during a medical procedure, which can be undesirable. Further, a cutting tool may be relatively sharp, and use of the tool in such close proximity to the catheter body may be undesirable.

In examples described herein, a balloon sheath is configured to be split longitudinally and removed from a balloon catheter. The balloon sheath may be referred to as a splittable balloon sheath or a splittable sheath. In some examples, the splittable sheaths may be split and removed from the catheter without the aid of a sharp cutting tool. A splittable sheath may include a sheath body and a sheath insert configured to be received within a channel defined by the sheath body. The channel may extend in a longitudinal direction at least partially between proximal and distal ends of the sheath body, such as only partially between the proximal and distal ends or along the entire length of the sheath body (from the proximal end to the distal end). In examples in which the channel extends only partially between the proximal and distal ends of the sheath body, the channel may, for example, extend from the proximal end of the sheath body to a location proximal to the distal end, or from the distal end of the sheath body to a location distal to the proximal end.

In examples in which the channel extends the full length of the sheath body, the balloon sheath may be configured to be fully split in the longitudinal direction to enable the balloon to be removed from around the catheter in a lateral direction (orthogonal to a longitudinal axis of the catheter). In examples in which channel extends only partially between the proximal and distal ends of the sheath body, the balloon sheath is configured to be only partially longitudinally split, and a clinician can use a cutting tool or manually pull the edges of the channel apart to fully split the balloon sheath and remove it from around the catheter in a lateral direction.

When the sheath body and the sheath insert are assembled together (e.g., by inserting the sheath insert into the channel), the sheath insert closes the channel and, as a result, closes a lumen defined by the sheath body. In this way, the sheath insert together with the sheath body defines a sheath that can enclose a balloon of a balloon catheter or another device. For example, in some examples, when the sheath insert is introduced into the channel of the sheath body, the sheath insert and the sheath body define a tubular sheath or a semi-tubular sheath, which may be generally tubular but for a few variations in the geometry due to how the sheath insert fits with the sheath body. In these examples, the sheath insert and the sheath body are coaxial parts of a tubular or semi-tubular body. When assembled together, a portion of the sheath insert may protrude into a lumen defined by the sheath body, such that the inner lumen defined by the splittable sheath is irregular (e.g., non-circular in cross-section). In other examples, the sheath insert may not protrude into a lumen defined by the sheath body, such that the assembled sheath defines a lumen having a more regular cross-section (e.g., circular in cross-section or nearly circular).

When the sheath insert is received within the channel of the sheath body, a clinician may split the splittable sheath by grasping the sheath body directly or by grasping a tab connected to the sheath body, and/or by grasping the sheath insert directly or by grasping a tab connected to the sheath insert, and removing the sheath insert from the channel. For example, the clinician may pull the sheath insert in a direction away from the sheath body to slide the sheath insert out of the channel, may pull the sheath body in a direction away from the sheath insert, or any combination thereof. After the sheath insert is removed from the channel of the sheath body, the sheath body is at least partially longitudinally split along the channel. In this way, the example splittable sheaths described herein are configured to split along a predetermined path defined by the channel of the sheath body. This splitting of the sheath along a predetermined path may enable a clinician to better predict how the sheath body will operate during use. The clinician may use this information to, for example, orient the sheath body relative to a catheter, patient, or the clinician during a medical procedure, e.g., to reduce the time required to perform the medical procedure.

While the present disclosure describes devices including balloon catheters and splittable sheaths primarily in the context of angioplasty procedures for treating atherosclerosis, the devices of the present disclosure may also be used for restoring patency to other lumens within the body of a patient, such as a lumen of a fallopian tube, urethra, esophagus, bile duct, or other anatomical structure. Further, the splittable sheaths described herein may be used with medical device other than balloon catheters, such as a self-expandable medical device (e.g., a self-expandable stent), or some example atherectomy devices.

FIGS. 1-3 illustrate an example medical device 10 that may be used alone or in conjunction with other medical devices, such as introducer sheaths. FIG. 1 is a side view of the medical device 10, which is configured for use in a medical procedure to restore adequate blood flow to a target vessel within the body of a patient. The medical device 10 includes a splittable sheath 12 and a catheter 14 including an expandable balloon 16. The splittable sheath 12 defines a lumen 20 and includes a sheath body 18 and a sheath insert 22. The sheath body 18 extends between a distal end 26 and a proximal end 28, and includes a sheath body tab 24 and an outer wall 30 that defines a channel 32 (not visible in the example shown in FIG. 1, but discussed below with respect to FIG. 4B) that is configured to receive the sheath insert 22. In some examples, a proximal end 29 of the sheath insert 22 is axially aligned (along the longitudinal axis 35) with the proximal end 28 of the sheath body 18 when the sheath 12 is in the assembled configuration shown in FIG. 1.

The lumen 20 of the splittable sheath 12 may be defined only by the sheath body 18 when the sheath insert 22 is not received within the channel 32, and may be defined both by the sheath body 18 and the sheath insert 22 when the sheath insert 22 is received within the channel 32. The lumen 20 has a length $L_L$ (the length $L_L$ being measured along a longitudinal axis 35 of the device 10) that is selected to receive the expandable balloon 16 having a length $B_L$ (also measured along the longitudinal axis 35). The longitudinal direction extends in the y-axis direction, where orthogonal x-y axes are shown in FIG. 1, and other orthogonal axes are shown in the other figures, for ease of description only. Further, the orthogonal x-y-z axes shown in the figures provide a common frame of reference for the different views of the devices described herein.

In the example of FIG. 1, the sheath body tab 24 extends proximally from the proximal end 28 of the sheath body 18. The sheath insert 22 includes a sheath insert tab 34 that extends proximally from the proximal end 29 of the sheath insert 22. In other examples, the sheath body tab 24 and the sheath insert tab 34 may extend distally from the sheath body 18 and the sheath insert 22, respectively. The tabs 24, 34 may be integrally formed with the sheath body 18 and the sheath insert 22, respectively, or may be formed separately form the sheath body 18 and the sheath insert 22, and affixed to respective ones of the sheath body 18 and the sheath insert 22. In some examples, the tabs 24, 34, as well as other tabs of splittable sheaths described herein, may be formed from different materials than the sheath body 18, or may be formed from the same materials the sheath body 18, but may also include an additional layer. The additional layer may, for example, help increase the friction of the tabs 24, 34, which may help facilitate gripping of the tabs 24, 34 by a clinician. For example, the additional layer may be a material that is more tacky or provides more friction when interfacing with surgical gloves.

Although FIG. 1 illustrates the splittable sheath 12 including the tabs 24, 34, in other examples, the splittable sheath 12 may include only one of the tabs 24, 34 (e.g., either the sheath body tab 24 or the sheath insert tab 34), or may not include any tabs protruding from an end of the splittable sheath 12 (e.g., from an end of the lumen 20).

The catheter 14 includes a catheter body 36 having a proximal end 38, and a hub 40 positioned at the proximal end 38 of the catheter body 36. The expandable balloon 16 is carried by the catheter body 36 of the catheter 14, and can be positioned at any suitable longitudinal position along the catheter body 36. In the example shown in FIG. 1, the expandable balloon 16 is positioned at a distal portion of the catheter body 36. In some examples, the expandable balloon 16 is fixedly attached to the catheter body 36, such as by adhesives, solder, overmolding welding, or other suitable fixation mechanisms, so that the expandable balloon 16 may remain securely attached to the catheter body 36 when the expandable balloon 16 is inflated at the target site.

In some examples, the lumen 20 of the splittable sheath 12 may be sized to substantially enclose the expandable balloon 16 while enabling the expandable balloon 16 to be longitudinally moveable within the lumen 20. For example, a greatest cross-sectional dimension (e.g., a diameter) of the lumen 20 may be equal to or larger than a greatest cross-sectional dimension (e.g., a diameter) of the expandable balloon 16 when the expandable balloon 16 is in an unexpanded configuration, the cross-sections being taken in a direction orthogonal to longitudinal axis 35. In some such examples, the cross-sectional dimension of the lumen 20 may be sufficiently larger than the cross-sectional dimension of the expandable balloon 16 to enable the expandable balloon 16 to be readily slidable within the lumen 20 when a clinician moves the catheter 14 proximally or distally relative to the splittable sheath 12, which may help substantially maintain the integrity of a drug coating that may be included on the expandable balloon 16 while the expandable balloon 16 is received within the lumen 20. In other examples, the greatest cross-sectional dimension (e.g., a diameter) of the lumen 20 may be substantially equal or slightly less than the greatest cross-sectional dimension (e.g., a diameter) of the balloon 16 in an unexpanded configuration (e.g., examples in which the balloon 16 does not include a drug coating). In such examples, the balloon 16 may exert sufficient force on one or more inner surfaces of the sheath body 18 and the sheath insert 22 to increase the fixation between the sheath body 18 and the sheath insert 22 when the sheath insert 22 is received within the channel 32 and the balloon 16 is received within the lumen 20.

In some examples, the splittable sheath 12 may include a lubricious material along the lumen 20, the lubricious material being configured to reduce friction between the balloon 16 and an inner surface of the splittable sheath 12 defining the lumen 20. In such examples, the inner surface of the sheath body 18 and/or the sheath insert 22 may be coated with a material having a relatively low coefficient of friction relative to the balloon 16, or a material of one or both of the sheath body 18 and the sheath insert 22 may have a relatively low coefficient of friction relative to the balloon 16. Such materials (e.g., PTFE or the like) may help preserve the integrity of a drug coating that may be included on the expandable balloon 16. Reducing the friction between the inner surface of the splittable sheath 12 defining the lumen 20 and the balloon 16 may help substantially maintain the integrity of a drug coating that may be included on the outer surface of the expandable balloon 16 by at least reducing the amount of drug coating that is inadvertently removed by the splittable sheath 12.

In some examples, the length $L_L$ of the lumen 20 may be sufficient to enclose at least a majority of a length $B_L$ of the expandable balloon 16, such as about 100% of the length $B_L$ of the balloon 16, or about 60% to about 95% of the length $B_L$ of the expandable balloon 16. In addition, in some examples, the length $L_L$ of the lumen 20 may be sufficient to fully enclose the length $B_L$ of the expandable balloon 16, such that the length $L_L$ may be about 100% to about 125% of the length $B_L$ of the expandable balloon 16. Configuring the splittable sheath 12 to substantially enclose the length $B_L$ of the expandable balloon 16 while also enabling the expandable balloon 16 to be longitudinally moveable within the lumen 20 may help prevent a clinician or other use from inadvertently contacting the expandable balloon 16 prior to introduction of the expandable balloon 16 into the vasculature of a patient.

The splittable sheath 12 is configured to contain the expandable balloon 16 within the lumen 20 until the expandable balloon 16 is advanced out of the lumen 20. A clinician may, for example, advance the balloon 16 (and the catheter body 36) distally until the balloon 16 exits the lumen 20 and enters the vasculature of a patient, or, in some examples, into an introducer sheath that has been inserted into the vasculature of the patient through the patient's skin.

In some cases, it may be advantageous to retain the splittable sheath 12 on the catheter body 36 and over the balloon 16 until the balloon 16 has been advanced out of the lumen 20, e.g., into an introducer sheath or the vasculature of a patient. For example, retaining the splittable sheath 12 on the catheter body 36 until the expandable balloon 16 has been advanced distally into an introducer sheath or the vasculature of a patient may help protect the structural integrity of the expandable balloon 16 and any drug coatings thereon by shielding the expandable balloon 16 from direct physical contact with the external environment prior to introduction of the expandable balloon 16 into the patient's body. In some examples, the splittable sheath 12 also may serve to stabilize and guide the expandable balloon 16 as it is being advanced into an introducer sheath or into the patient's body. Thereafter, it may be advantageous to remove the splittable sheath 12 from the catheter body 36, to enable an entire length of the catheter body 36 to be advanced through an introducer sheath or directly into the patient vasculature. In other examples, the splittable sheath 12 may be removed from the catheter body 36 prior to introduction of the expandable balloon 16 into the patient's body, or may be retained on the catheter body 36 after the expandable balloon has been introduced into the patient's body.

As discussed in further detail with respect to FIGS. 4A-10B, the splittable sheath 12 is configured split into multiple parts, e.g., the sheath body 18 and the sheath insert 22, along a predetermined path, such that the splittable sheath 12 may be easily and predictably separated and removed from over catheter 14. In some cases, it may be advantageous for a clinician to be able to split the balloon sheath 12 and remove the sheath 12 from over the catheter 14 during a procedure to advance the expandable balloon 16 to a target site within the vasculature. For example, configuring the splittable sheath 12 to be removable from over the catheter 14 may enable a clinician to advance a greater portion of a length of the catheter 14 into the vasculature of the patient than would be practicable if the sheath 12 were not easily removeable from the catheter 14, or at least minimize the length of the catheter body 36 needed for a medical procedure. As discussed above, in example medical devices having a balloon sheath that is not configured to be removable from over a catheter, a portion of the catheter equal to a length of a body of the balloon sheath may be operationally unusable in order to accommodate the placement of the balloon sheath over the catheter body, even after the balloon sheath is no longer positioned over the balloon of the catheter. Thus, the splitting and removal from a catheter of the splittable sheaths described herein, such as the splittable sheath 12, may enable substantially an entire length of the catheter body 36 to be operationally usable, including a length of the catheter body 36 housed within the splittable sheath 12 when the expandable balloon 16 is received within the lumen 20.

FIG. 2 is a cross-sectional view of the catheter 14 taken along the line A-A in FIG. 1, which extends orthogonally to the longitudinal axis 35 of the device 10. As shown in FIG. 2, the catheter 14 includes an inflation lumen 42. The catheter 14 may also include a guidewire lumen 44 configured to receive a guidewire 46. During use of the medical device 10, the guidewire 46 may be introduced into the vasculature of a patient, and then the catheter body 36 may be navigated over the guidewire 46 to the target site.

In some examples, the guidewire lumen 44 may extend longitudinally through the catheter 14 from a distal portion of the catheter body 36 to the hub 40 positioned at the proximal end 38 of the catheter 14. The hub 40 may include a first port that provides access to the guidewire lumen 44 to enable a clinician to advance the catheter body 36 along the guidewire 46. Similarly, the inflation lumen 42 may extend longitudinally through the catheter 14 from the hub 40 to the expandable balloon 16. The hub 40 may include a second port that provides access to the inflation lumen 42. In some examples, the inflation lumen 42 terminates distally at an opening to the interior of the expandable balloon 16. The inflation lumen 42 may be configured to receive a fluid that is introduced into the inflation lumen 42 from the hub 40 to expand or inflate the expandable balloon 16 (e.g., once the expandable balloon 16 has been navigated to the target site).

FIG. 3 is a side view of the catheter 14 with the splittable sheath 12 removed from around the expandable balloon 16, and illustrates the expandable balloon 16 positioned on the catheter body 36 in an unexpanded configuration. In some examples, the expandable balloon 16 includes a coating on an outer surface 48 of the expandable balloon. As depicted in FIG. 3, the expandable balloon 16 is in a deflated state, and is folded or rolled into a physically smaller profile (e.g., smaller than an inflated state of the expandable balloon 16). The general shape of the deflated state of the expandable balloon 16 shown in FIG. 3 is for illustration purposes only; other shapes and configurations of the expandable balloon 16 in a deflated state are also possible. For example, balloon 16 may be folded over itself in the deflated state. Further, as depicted in FIG. 3, the guidewire 46 may extend through the guidewire lumen 44 of the catheter body 36, from a position distal to the expandable balloon 16 longitudinally through the catheter 14 to the hub 40.

The expandable balloon 16 may be formed from any suitable material that provides sufficient strength and flexibility for the pressures experienced by the expandable balloon 16 during the inflation procedure and during a medical procedure. The materials from which the expandable balloon 16 is formed may be biocompatible and compatible (i.e., chemically non-reactive) with a drug coating on the outer surface 48 of the expandable balloon 16. In some examples, materials from which the expandable balloon 16 is formed may include nylon, polyethylene terephthalate (PET), polyethylene (such as crosslinked polyethylene), polyurethane, polyvinyl chloride, silicone elastomer, or the like.

The coating on the outer surface 48 of the balloon 16 may be any suitable coating that facilitates use of balloon 16, a medical procedure, or the like. In some examples, the coating may include, for example, a lubricious coating (either hydrophilic or hydrophobic), a drug coating, or the like. In some examples, the drug coating may include a pharmacologically-active agent selected to treat vascular disease, such as an anticoagulant, anti-inflammatory agent, antiproliferative, or other agent or drug. For example, the anti-proliferative drug paclitaxel may be used in coronary angioplasty procedures to help reduce unwanted cell growth. In some examples, the drug coating may further include an excipient to facilitate release of the drug from the drug coating. Example excipients include urea, polysorbate, sorbitol, or other suitable agents.

Figure 4B:
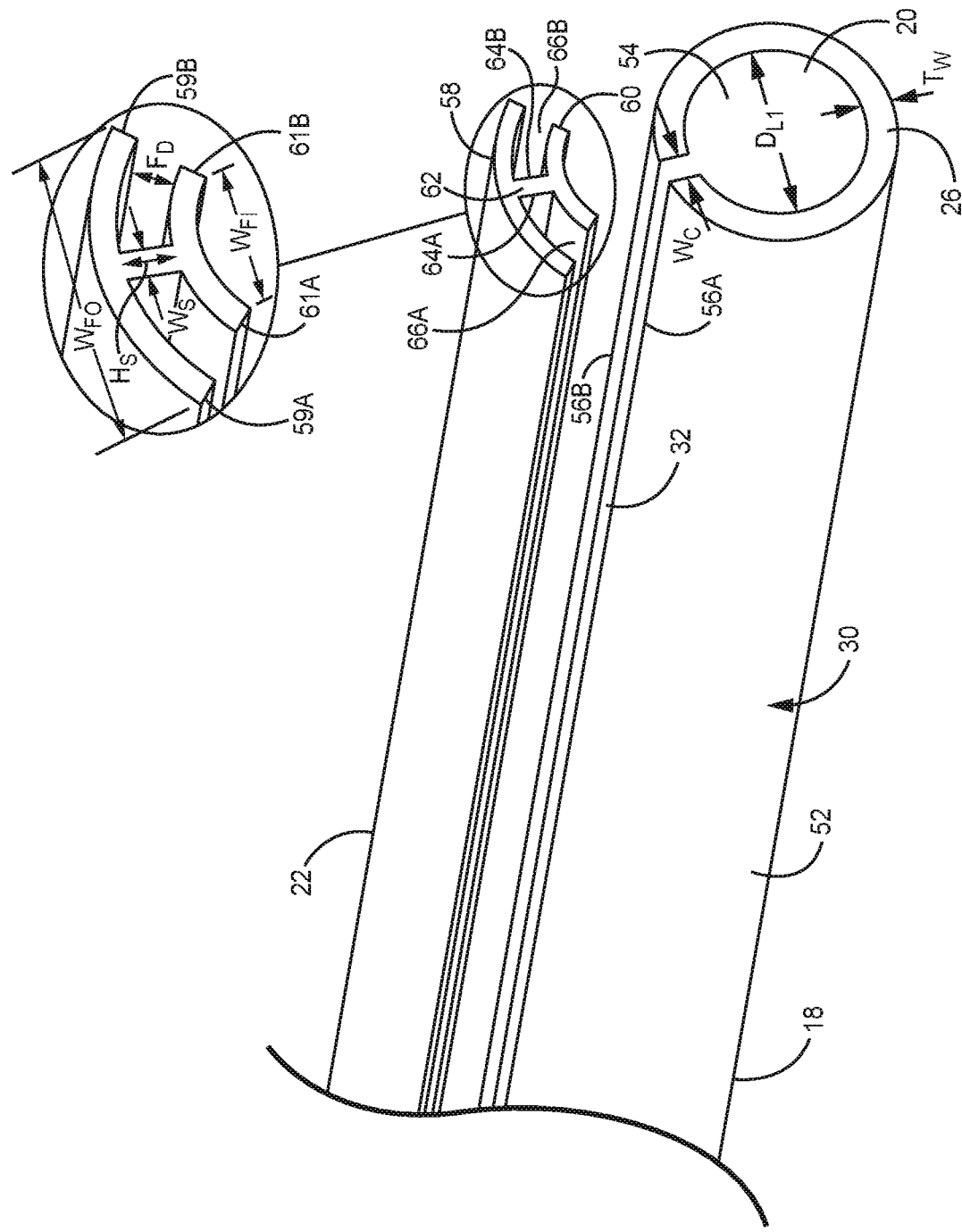
FIG. 4B is an exploded view of the splittable sheath of FIG. 4A, and illustrates a sheath insert of the splittable sheath separated from a sheath body of the splittable sheath.

FIGS. 4A and 4B illustrate an example of the splittable sheath 12 of the medical device 10 of FIGS. 1-3. FIG. 4A is a perspective view of the splittable sheath 12 in an assembled configuration, and FIG. 4B is an exploded view of the splittable sheath 12, in which the sheath body 18 and the sheath insert 22 are not assembled together.

As shown in FIG. 4B, the outer wall 30 of the sheath body 18 defines a channel 32, in which the sheath insert 22 is configured to be received in order to assemble the sheath body 18 and the sheath insert 22 together to form the assembled sheath 12 shown in FIG. 4A. The outer wall 30 of the sheath body 18 further defines an outer surface 52 and an inner surface 54. The inner surface 54 of the outer wall 30 of the sheath body 18 partially defines the lumen 20 of the sheath 12. The sheath body 18 may be formed using any suitable technique, such as, but not limited to, extrusion of the sheath body 18 and subsequent removal of material from the sheath body 18 to define the channel 32, injection molding, other molding techniques, or the like. When the sheath insert 22 is received within the channel 32, the sheath insert 22 closes the channel 32 and defines remaining portion of the lumen 20.

The channel 32 is defined between a first edge 56A and a second edge 56B of the sheath body 18. The channel 32 extends through a thickness $T_W$ of the outer wall 30 of the sheath body 18 from the outer surface 52 to the inner surface 54, and, in the example shown in FIG. 4B, extends longitudinally from the distal end 26 to the proximal end 28 of the sheath body 18. In other examples, however, the channel 32 may extend longitudinally only partially between the distal end 26 and the proximal end 28 of the sheath body 18. In examples in which the channel 32 extends only partially between the distal end 26 and the proximal end 28 of the sheath body, the channel 32 may extend from the proximal end 28 to a location proximal to the distal end 26, or from the distal end 26 to a location distal to the proximal end 28.

In the example shown in FIGS. 4A and 4B, the sheath insert 22 includes an outer flange 58, an inner flange 60, and a septum 62 extending between the outer flange 58 and the inner flange 60. The sheath insert 22 may be formed using any suitable technique, such as, but not limited to, injection molding, other molding techniques, extrusion, and the like. The septum 62 is configured to be received within the channel 32 when sheath 12 is in its assembled configuration. The outer flange 58 and the inner flange 60 each extend away from the septum 62 (on opposite sides of the septum 62) in a direction generally orthogonal to the central longitudinal axis 35 of the sheath 12. Thus, when the septum 62 is introduced in the channel 32, the outer flange 58 is adjacent to the outer surface 52 of the sheath body 18 and outside of the lumen 20, and the inner flange 60 is adjacent the inner surface 54 of the sheath body 18.

The septum 62 and the flanges 58, 60 are configured to help maintain the splittable sheath 12 in an assembled configuration until a clinician begins to split the splittable sheath 12. For example, when the septum 62 is received within the channel 32, the flanges 58, 60 are configured to help retain the septum 62 within the channel 32 by at least minimizing or even preventing movement of the sheath insert 22 relative to the sheath body 18 in a direction orthogonal to the central longitudinal axis 35. The flanges 58, 60 help prevent such movement of the sheath insert 22 because the flanges 58, 60 have widths $W_{FO}$, $W_{FI}$, respectively, greater than a width $W_C$ of the channel 32 when the septum 62 is introduced in the channel 32. Engagement of outer flange 58 with outer surface 52 of the sheath body 18 helps to prevent movement of the sheath insert 22 into the lumen 20 (or the part of the lumen defined by the sheath body 18), and engagement of the inner flange 60 with the inner surface 54 of the sheath body 18 helps to prevent movement of the sheath insert 22 in a direction away from the sheath body 18. Widths $W_{FO}$ and $W_{FI}$ are measured along respective straight lines extending from a first side to a second side of the respective flange 58, 60, the first and second sides of a flange being opposite sides of the septum 62.

The flanges 58, 60 may have any suitable configuration for retaining the septum 62 in the channel 32. The outer flange 58 defines ends 59A and 59B, and the inner flange 60 defines ends 61A, 61B. The respective ends 59A, 59B and 61A, 61B of the flanges 58, 60 may have any suitable cross-sectional shape (the cross-section being taken in a plane orthogonal to the longitudinal axis 35), and may be blunt and/or have substantially squared-off shapes, as illustrated in FIG. 4B. In other examples, one or more of the septum 62 or the ends 59A, 59B and 61A, 61B of the flanges 58, 60 may have other shapes, as described below with respect to FIGS. 7A-9E.

In some examples, the shapes of the flanges 58, 60 in a cross-section of the sheath insert 22 (taken orthogonally to the longitudinal axis 35) each may be curvilinear in profile. The curvilinear profile may match the profile of the outer surface 52 and the inner surface 54 of the sheath body 18 in some examples. As illustrated in FIG. 4B, this curvilinear shape enables the flanges 58, 60 respectively to conform to the outer surface 52 and the inner surface 54 of the outer wall 30 of the sheath body 18 when the sheath insert 22 is received within the channel 32. In this manner, the flanges 58, 60 may be configured to sit flush against the outer surface 52 and the inner surface 54 of the outer wall 30, providing a close fit between the sheath body 18 and the sheath insert 22, thereby enhancing the stiffness of the splittable sheath 12 when the sheath 12 is in the assembled configuration. In addition, the flanges 58, 60 sitting flush against the outer surface 52 and the inner surface 54 of the outer wall 30 may strengthen the mechanical connection between the sheath body 18 and the sheath insert 22.

In some examples, the outer flange 58 may extend along the outer surface 52 of the outer wall 30 to proportionately the same extent (e.g., percentage of the outer surface 52) that the inner flange 60 extends along the inner surface 54 of the outer wall 30 of the sheath body 18. In other examples, the outer flange 58 and outer flange 60 may extend along different extents of the respective surfaces 52, 54 of the outer wall 30. In either case, the widths $W_{FO}$ and $W_{FI}$ of the respective flanges 58, 60 may be selected based on the outer and inner dimensions of the sheath body 18. For example, the sheath body the widths $W_{FO}$ and $W_{FI}$ may be selected such that when the sheath insert 22 is received within the channel 32 of the sheath body 18, the outer flange 58 extends along about 10% to about 25% of a perimeter of the outer surface 52 of the outer wall 30, and the inner flange extends along about 10% to about 25% of a perimeter of the inner surface 54 of the outer wall 30.

The widths $W_{FO}$ and $W_{FI}$ of the flanges 58, 60, respectively, may also be selected based on other considerations, such as a desired degree of stiffness of the splittable sheath 12, or a desired dimension of the lumen 20 when the sheath insert 22 is received within the channel 32. For example, large values of the widths $W_{FO}$ and $W_{FI}$ may increase an overall stiffness of the splittable sheath 12 by providing a relatively larger area of overlap between the outer wall 30 of the sheath body 18 and the flanges 58, 60. The overlap between the sheath body 18 and the flanges 58, 60 of the sheath insert 22 may contribute to the stiffness of the assembled sheath 12.

In the example illustrated in FIG. 4B, the septum 62 and the flanges 58, 60 of the sheath insert 22 define form a modified "I" shape in cross-section (the cross-section being taken in direction orthogonal to the longitudinal axis 35). The septum 62 form a substantially straight center portion of the "I" shape, while the flanges 58, 60 respectively form the top and bottom portions of the "I" shape, though not necessarily to the scale of corresponding portions of a letter "I." A first slot 66A is formed by a space between the outer flange 58, the inner flange 60, and the first surface 64A of the septum 62, and a second slot 66B is formed by a space between the outer flange 58, the inner flange 60, and the second surface 64B of the septum 62. The slots 66A, 66B are configured to receive the edges 56A, 56B of the sheath body 18.

As shown in FIG. 4B, the septum 62 defines a first surface 64A and a second surface 64B that engage with respective edges 56A, 56B of the sheath body 18 when the sheath insert 22 is introduced in the channel 32 and the edges 56A, 56B of the sheath body 18 are introduced in the slots 66A, 66B. The distance between the first surface 64A and the second surface 64B represents a width $W_S$ of the septum 62. In some examples, the septum width $W_S$ may be from about 0.20 millimeters to about 2.00 millimeters. However, other dimensions may also be used in other examples and may be selected based on the size of the desired sheath 12. A width $W_S$ of the septum 62 may be affect the amount of force required to remove the sheath insert 22 from the sheath body 18. For example, relatively larger widths $W_S$ of septum 62 may result in the sheath insert 22 being more difficult to remove from the sheath body 18 than examples in which the septum 62 has a relatively smaller width $W_S$.

In some examples, the septum 62 (as well as other septums described herein) and/or the sheath body 18 (as well as other sheath bodies described herein) may include a lubricious material (e.g., a coating or a surface treatment) to reduce the friction between the septum 62 and the sheath body 18 and aid the removal of the sheath insert 22 from the sheath body 18. For example, a lubricious coating may be applied to the first surface 64A and/or the second surface 64B of the septum 62. Example lubricious coatings or materials includes PTFE or other polymer based materials.

The dimensions of one or more of the components of the splittable sheath 12 may be selected based on a desired strength of a mechanical connection between the sheath body 18 and the sheath insert 22 when the splittable sheath 12 is assembled. For example, a dimension $F_D$ of one or both slots 66A or 66B, measured between an inner surface of the outer flange 58 and an outer surface of the inner flange 60, may be less than or equal to a thickness $T_W$ of the outer wall 30 of the sheath body 18. In other examples, dimension $F_D$ of a slot 66A or 66B may be greater than a thickness $T_W$ of the outer wall 30 of the sheath body 18.

A dimension $F_D$ that is less than the thickness $T_W$ of the outer wall 30 of the sheath body 18 may enable portions of the outer wall 30 received within the slots 66A, 66B of the sheath insert 22 to be more readily slidable (e.g., for a given pulling or push force to the sheath insert 22) within the slots 66A, 66B when the splittable sheath 12 is in the assembled configuration of FIG. 4A. Thus, a dimension $F_D$ that is less than the thickness $T_W$ of the outer wall 30 of the sheath body 18 may better facilitate separation of the sheath 12 into multiple parts 18, 22. However, a dimension $F_D$ that is equal to or greater than the thickness $T_W$ of outer wall 30 of the sheath body 18 may enable a better mechanical interference fit between the sheath body 18 and the sheath insert 22 when the splittable sheath 12 is in the assembled configuration of FIG. 4A, and, therefore, better structural integrity of the assembled sheath 12.

In some examples, the thickness $T_W$ of the outer wall 30 of the sheath body 18 may be from about 0.20 millimeters to about 0.30 millimeters, although other thicknesses $T_W$ of the outer wall 30 may be possible depending upon one or more other dimensions of the splittable sheath 12 or the balloon 16.

The dimension $F_D$ of a slot 66A or 66B may depend on the height $H_S$ of the septum 62, also measured between the inner surface of the outer flange 58 and the outer surface of the inner flange 60. In some examples, the dimension $F_D$ of a slot 66A or 66B is the same as the height $H_S$ of the septum 62, while in other examples, the $F_D$ of a slot 66A or 66B is greater than the height $H_S$ of the septum 62 due to the way in which the flanges 58, 60 extend away from the septum 62.

In some examples, a space between the first edge 56A and the second edge 56B of the sheath body 18 that defines the channel 32 may have a width $W_C$ when the sheath insert 22 is not received within the channel 32 and in the absence of other externally applied forces (e.g., from the sheath insert 22, a clinician, or the like) pulling the edges 56A, 56B apart. That is, the width $W_C$ represents a width of the channel 32 when the sheath body 18 is in an at-rest state. The channel 32 and the septum 62 may have any suitable relatively dimensions, which may be selected based on a desired fit between the sheath insert 22 and the sheath body 18 when the splittable sheath 12 is in the assembled configuration.

In some examples, the width $W_C$ of the channel 32 may be less than the septum width $W_S$. In such examples, when the septum 62 of the splittable sheath 12 is introduced into the channel 32, the sheath body 18 is deformed to increase the width $W_C$ of the channel 32 to a width greater than or equal to the septum width $W_S$ in order to enable the septum 62 to be introduced into the channel 32 and close the channel 32. With the sheath insert 22 received within the sheath body 18 (as shown in FIG. 4A), the first edge 56A of the sheath body 18 may be received within the first slot 66A of the sheath insert 22 and positioned in contact with the first surface 64A of the septum 62, and the second edge 56B of the sheath body 18 may be received within the second slot 66B of the sheath insert 22 and positioned in contact with the second surface 64B of the septum 62.

In other examples, the width $W_C$ of the channel 32 is greater than or equal to the septum width $W_S$. In examples in which the width $W_C$ of the channel 32 is greater than the septum width $W_S$, the channel 32 may be closed by both the septum 62 and the flanges 58, 60 when the sheath insert 22 is received within the channel 32. That is, even in examples in which the edges 56A, 56B of the sheath body 18 are not necessarily in contact with respective ones of the surfaces 64A, 64B of the septum 62 when the edges 56A, 56B are positioned within respective ones of the slots 66A, 66B, the splittable sheath 12 may be retained in an assembled configuration when the sheath insert 22 is received within the channel 32.

A width $W_S$ of the septum 62 is less than the widths $W_{FO}$, $W_{FI}$ of at least one of the flanges 58, 60, and, as discussed above, the widths $W_{FO}$, $W_{FI}$ of the flanges 58, 60 are greater than a width of the channel 32 when the septum 62 is received within the channel 32. Thus, when the septum 62 of the sheath insert 22 is received within the channel 32, the outer flange 58 may extend outwardly from the channel 32 along the outer surface 52 of the outer wall 30, and the inner flange 60 may extend outwardly from the channel 32 along the inner surface 54 of the outer wall 30. The outward extension of the flanges 58, 60 from the channel 32 along the respective surfaces 52, 54 of the outer wall 30 may limit movement of the sheath insert 22 relative to the longitudinal axis 35 when the sheath insert 22 is received within the channel 32. In this manner, the outer flange 58 and the inner flange 60 may help retain the sheath insert 22 within the sheath body 18 when the splittable sheath 12 is in the assembled configuration, such as by helping to prevent the sheath insert 22 from being displaced from the channel 32 in a direction orthogonal to the longitudinal axis 35. Thus, although slight radial movement of the sheath insert 22 within the sheath body 18 (e.g., movement that may occur during delivery of the balloon 16 through the lumen 20), may cause the inner flange 60 to be moved against the inner surface 54 of the outer wall 30, but not cause the sheath insert 22 to be inadvertently removed from the channel 32 during a medical procedure.

In addition to or instead of the relative dimensions of the sheath body 18 and the sheath insert 22, the shapes of one or more components of the splittable sheath may be selected based on a desired strength of a mechanical union between the sheath body 18 and the sheath insert 22. For example, as discussed above, the inner surfaces of the outer flange 58 may have a curved shape that is configured to substantially conform to a curvature of the outer surface 52 of the outer wall 30, and the inner surfaces of the inner flange 60 may have a curved shape that is configured to substantially conform to a curvature of the inner surface 54 of the outer wall 30. In such examples, the conformation of one or more surfaces of the flanges 58, 60 to one or more surfaces of the sheath body 18 may further help to maintain the mechanical union between the sheath body 18 and the sheath insert 22 when the splittable sheath 12 is in the assembled configuration of FIG. 4A.

Relatively movement of the sheath body 18 and the sheath insert 22 when sheath 12 is assembled can be minimized or even prevented using any suitable technique. In the assembled configuration of the sheath 12, the septum 62 of the sheath insert 22 constrains rotation of the sheath insert 22 relative to the sheath body 18, and the flanges 58, 60 can act as a radial constraint on the sheath insert 22 in the plane normal to a longitudinal axis of the sheath. Relative movement between the sheath body 18 and the sheath insert 22 can also be minimized or event prevented using other suitable techniques, such as, but not limited to, mating features, interference fits, adhesive, tape, or any combination thereof.

Relative longitudinal movement between the sheath body 18 and sheath insert 22 until the clinician is ready to split the sheath may be minimized using any suitable technique. In some examples, a radially outward force applied by the balloon 16 or other medical device within a lumen 20 of the splittable sheath 12 may increase a strength of the interference fit between the sheath body 18 and the sheath insert 22. In these examples, after a clinician has advanced the balloon (or other medical device) through the lumen 20 of the splittable sheath 12, the strength of interference fit between the sheath body 18 and the sheath insert 22 may be decreased, thereby enabling the clinician to more easily remove the sheath insert 18 from the channel of the sheath body than when the balloon 16 is received within the lumen 20.

In addition to or instead of a radially outward force applied by a device within the lumen 20 of the sheath 12, the longitudinal shape of the sheath body 18 and the sheath insert 22 can be selected to minimize relative longitudinal movement between the sheath body 18 and the sheath insert 22. For example, as described with respect to FIGS. 6A and 6B, the channel 32 defined by the sheath body 18 may have a wedge shape and the sheath insert 22 may have a corresponding wedge shape. The wedge shapes may increase the inward biasing force applied by the sheath body 18 on the sheath insert 22 when the sheath insert 22 is inserted in the channel 32, thereby improving the longitudinal cohesion between the sheath body 18 and the sheath insert 22.

When the sheath insert 22 is received within the channel 32 of the sheath body 18, a clinician may split the splittable sheath 12 by separating the sheath body 18 from the sheath insert 22. For example, the clinician may move a first portion of the splittable sheath 12 (e.g., the sheath body 18 or the sheath insert 22) away from a second portion of the splittable sheath 12 (e.g., the other one of the sheath body 18 or the sheath insert 22) to slide the sheath insert 22 out of the channel 32 of the sheath body 18. The clinician may, for example, pull the sheath insert 22 or the sheath body 18 in an outward direction 50 or in a proximal direction or a distal direction while holding the other one of the sheath insert 22 or the sheath body 18 stationary or pulling the other one of the sheath insert 22 or the sheath body 18 in an opposite direction. A clinician may choose to separate the sheath insert 22 from the sheath body 18 in one manner over another based on, for example, the presence of any physical obstacles present within a space surrounding the device 10 during a medical procedure.

As a clinician pulls the sheath insert 22 out of the channel 32 defined in the sheath body 18, a split in the splittable sheath 12 will form and lengthen. The split that forms in the splittable sheath 12 is the channel 32. Thus, "splitting" the splittable sheath 12 includes separating the sheath insert 22 from the sheath body 18 to expose the channel 32, and introduction of the sheath insert 22 into the channel 32 closes the split in the splittable sheath 12. After the sheath insert 22 is removed from the channel 32 of the sheath body 18, the sheath body 18 is at least partially longitudinally split along the channel 32, substantially parallel to the longitudinal axis 35. Once the sheath body 18 and the sheath insert 22 have been completely separated from one another, the sheath body 18 may remain positioned over the catheter body 36 (e.g., examples in which the width $W_C$ of the channel 32 is smaller than a diameter of the catheter body 36). In other examples, such as examples in which the width $W_C$ of the channel 32 is larger than a diameter of the catheter body 36, the sheath body 18 may not remain positioned over the catheter body 36 after the sheath body 18 and the sheath insert 22 have been completely separated from each other.

The multi-part construction of the splittable sheath 12 enables the splittable sheath 12 to be split along a predetermined path defined by the channel 32, such that the splittable sheath 12 may be easily and predictably separated and removed from over catheter body 36. This splitting of the splittable sheath 12 along a predetermined path may enable a clinician to better predict how the sheath body 18 will operate during use. The clinician may use this information to, for example, orient the sheath body relative to a catheter, patient, or the clinician during a medical procedure, e.g., to reduce the time required to perform the medical procedure.

Further, the multi-part configuration of the splittable sheath 12 may enable variability of the structural integrity of the splittable sheath 12 (e.g., longitudinal cohesion of the sheath body 18 and the sheath insert 22), thereby enabling both enhanced retention of the splittable sheath 12 over the balloon 16 of the catheter 14 and the splitting of the splittable sheath 12. For example, after a clinician has advanced the expandable balloon 16 through the lumen 20 of the splittable sheath 12, the strength of an interference fit between the sheath body 18 and the sheath insert 22 may be decreased in response to the absence of the expandable balloon 16 within the lumen 20, thereby enabling the clinician to more easily remove the sheath insert 22 from the channel 32 of the sheath body 18 than when the expandable balloon 16 is received within the lumen 20. In this way, the variable strength of the interference fit between the sheath body 18 and the sheath insert 22 may enable a relatively stronger mechanical connection between the sheath body 18 and the sheath insert 22 when structural integrity of the splittable sheath 12 is desirable, and a relatively weaker mechanical connection between the sheath body 18 and the sheath insert 22 when splitting of the splittable sheath 12 is desirable.

The sheath body 18 and the sheath insert 22 may be made by any suitable technique, and may be formed from any suitable one or more materials, such as, but not limited to, PTFE (e.g., expanded PTFE (ePTFE)), a high-density polyethylene (HDPE), a low-density polyethylene (LDPE), a material of the amide family, such as a polyamide or a polyamide block copolymer (e.g., PEBAX or other member of the PEBA family), or combinations thereof. The materials and configuration of the sheath body 18 and the sheath insert 22 may be selected such that the splittable sheath 12 has sufficient stiffness to provide structural support to balloon 16, e.g., to resist kinking or excessive bending or rotation as the expandable balloon 16 and the catheter 14 are advanced through the lumen 20 of the splittable sheath 12, while also having sufficient flexibility or deformability to facilitate removal of the sheath body 18 from the catheter 14 after the clinician has separated the sheath insert 22 from the sheath body 18.

In some examples, a material of the sheath body 18 may be more flexible or deformable than a material of the catheter body 36, thereby enabling the material of the sheath body 18 to flex or deform in response to being forced into contact with the catheter body 36. For example, after the clinician has separated the sheath insert 22 from the sheath body 18 and begins to pass the catheter body 36 through the channel 32 to remove the sheath body 18 from the catheter body 36, the material of the sheath body 18 may flex or deform such that a dimension of the channel 32 (e.g., a width measured orthogonal to the longitudinal axis 35) may be sufficiently enlarged to allow the catheter body 36 to pass through the channel 32, thereby enabling the clinician to fully remove the sheath body 18 from the catheter 14.

A clinician may split the splittable sheath 12 by grasping the sheath body 18 directly or by grasping a tab connected to the sheath body 18, and/or by grasping the sheath insert 22 directly or by grasping a tab connected to the sheath insert 22, and removing the sheath insert 22 from the channel 32. Thus, as shown in FIGS. 4A and 4B, in some examples, the splittable sheath 12 may include tabs 24, 34 attached to the sheath body 18 and the sheath insert 22, respectively, in order to facilitate separation of the sheath body 18 and the sheath insert 22 from each other. For example, in the example of FIG. 4A, the sheath body tab 24 extends proximally from the proximal end 28 of the sheath body 18, and the sheath insert tab 34 forms a proximal portion of the sheath insert 22 and extends proximally of the proximal end 29 of the sheath insert 22 when the splittable sheath 12 is in the assembled configuration shown in FIG. 4A.

In some examples, the sheath body tab 24 may be formed integrally with the sheath body 18, such that both the outer wall 30 of the sheath body 18 and the sheath body tab 24 are manufactured from a single piece of material. In addition, in some examples, the sheath insert tab 34 may be formed integrally with the sheath insert 22, such that the sheath insert tab 34 and the sheath insert 22 are manufactured from a single piece of material. In other examples, one or both of the sheath body tab 24 and the sheath insert tab 34 may be formed separately from the sheath body 18 and the sheath insert 22, and may be mechanically connected to the respective one of the sheath body 18 or the sheath insert 22 using any suitable technique, such as, but not limited to, an adhesive, overmolding, chemical welding, ultrasonic welding, or another suitable chemical or mechanical connection mechanism.

In some examples, the sheath body tab 24 may have a substantially flat shape, as illustrated in FIG. 4A, while in other examples, the sheath body tab may have a curved cross-sectional shape (e.g., orthogonal to the longitudinal axis 35) that may be substantially similar to a portion of a curved cross-sectional shape (e.g., orthogonal to the longitudinal axis 35) of the sheath body 18. In examples in which the sheath insert tab 34 is formed integrally with the sheath insert 22, the sheath insert tab 34 may be a proximal portion of the sheath insert 22 itself, and thus may have a configuration that is substantially similar to the rest of the sheath insert 22. In any such examples, the sheath body tab 24 and the sheath insert tab 34 may be configured for grasping by a clinician, either with the clinician's hand or with a gripping tool, as the clinician moves one or both of the tabs 24, 34 to split the splittable sheath 12 by separating the sheath body 18 from the sheath insert 22.

The sheath body tab 24 and the sheath insert tab 34 may have any suitable length for aiding splitting of sheath body 18, the length being measured parallel to the central longitudinal axis 35 of the sheath 12 (in the y-axis direction). For example, the tabs 24, 34 may each may have a length of approximately about 20% to about 70% of a total length of the splittable sheath 12, such as about 50% of the length of the sheath 12 (the total length including the length of the tabs). For example, a total length of the splittable sheath 12 may be about 20 millimeters to about 350 millimeters, such that the tabs 24, 34 each may have a length of about 4 millimeters to about 245 millimeters, depending on the relative proportions of the tabs 24, 34 and the sheath body 18.

Although the example of the splittable sheath 12 shown in FIGS. 4A and 4B includes the sheath body tab 24 and the sheath insert tab 34, other examples of the splittable sheath 12 may include a single tab (e.g., only one of the tabs 24 or 34) or more than two tabs, which may extend either distally of the distal end 26 or proximally of the proximal end 28 of the sheath body 18. In examples in which the splittable sheath 12 includes only a single tab (e.g., the sheath insert tab 34), the clinician may grasp the sheath insert tab 34 with one hand (or tool) and grasp the sheath body 18 with the other hand (or a tool), and hold the sheath body 18 stationary while moving the sheath insert tab 34 away from sheath body 18 to split the splittable sheath 12 in any of the manners described above.

In other examples, the splittable sheath 12 may not include any tabs. In such examples, a clinician may directly grasp the sheath body 18 with one hand (or a tool) and directly grasp the sheath insert with the other hand (or a tool), and hold the sheath body 18 stationary while moving the sheath insert 22 away from sheath body 18 to split the splittable sheath 12 in any of the manners described above.

In some examples, a single sheath insert 22 may be usable with multiple sheath bodies 18 having varying inner dimensions Du of the lumen 20 when the sheath insert 22 is not received within the channel 32. That is, the sheath insert 22 may be configured to fit within channels defined by a plurality of different sheath bodies having different cross-sectional sizes (the cross-section being taken in a direction orthogonal to the longitudinal axis 35) and/or different lengths. The plurality of different sheath bodies may define similar sized channels such that the same sheath insert 22 can be used to close each of the channels (at different times) to form splittable sheaths 12. However, because the plurality of different sheath bodies have different sizes, the resulting splittable sheaths formed with the same sheath insert 22 have different sizes. In this manner, examples of the splittable sheath 12 having a range of inner dimensions $D_{L2}$ of the lumen 20 may be assembled to accommodate balloons 16 having a range of outer dimensions from a single sheath insert 22. In some examples, the inner dimension $D_{L2}$ of the lumen 20 may be from about 1.30 millimeters to about 2.00 millimeters, although the inner dimension $D_{L2}$ of the lumen 20 may be larger or smaller in other examples.

In other examples, a single sheath body 18 may be usable with a plurality of different sheath inserts 22 having varying thicknesses $T_S$ of the septum 62. In these examples, the lumen 20 of the splittable sheath 12 may vary based on the sheath insert 22 that is introduced in the channel 32. The greater the width $W_S$ of the septum 62, the greater the inner dimensions $D_{L2}$ of the lumen 20 of the resulting splittable sheath 12. The edges 56A, 56B of the sheath body 18 may extend further away from each other in order to accommodate septa having greater thicknesses $T_S$, which results in a larger sized lumen 20. A clinician may select the sheath insert 22 based on the desired sized of the lumen 20.

In some cases, it may be advantageous to produce splittable sheaths having a range of inner dimensions $D_{L2}$, but in which the dimensions of a component (e.g., a sheath insert or a sheath body) of the splittable sheath 12 are held constant. For example, manufacturing costs may be decreased when a given size of the sheath body 18 or the sheath insert 22 may be used to define a plurality of splittable sheaths having different inner lumen dimensions. In this manner, fewer components may need be produced to obtain a desired size range of splittable sheaths, as compared to examples in which the dimensions of both the sheath body and the sheath insert are varied to produce different examples of the splittable sheath.

Figure 5A:
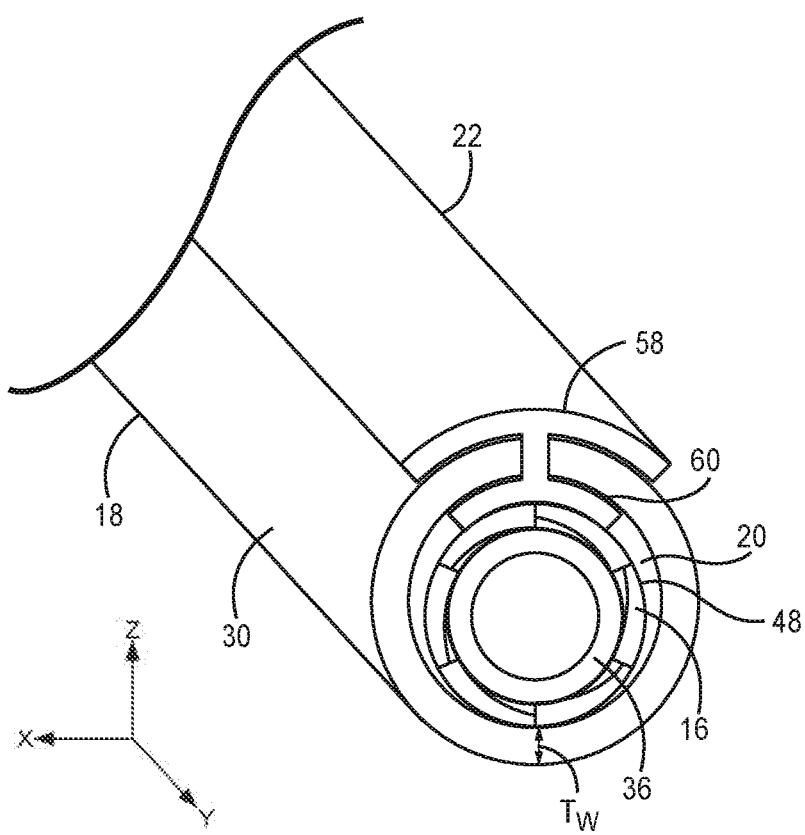
FIG. 5A is a perspective view of distal end of the device of FIG. 1, and illustrates the sheath insert received within a channel of the sheath body and the balloon received within a lumen of the splittable sheath.
Figure 5B:
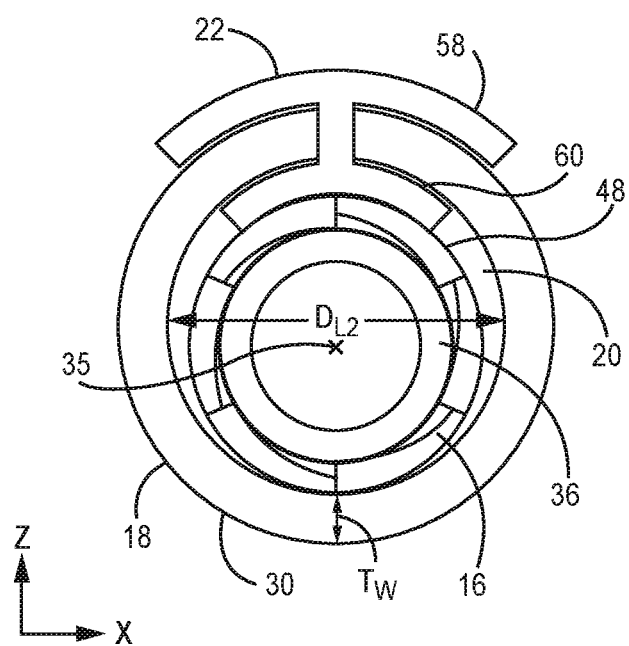
FIG. 5B is an end view of the device of FIG. 5A.

FIGS. 5A and 5B illustrate the splittable sheath 12 with the balloon 16 received within the lumen 20 of the splittable sheath 12. FIG. 5A is a perspective view of the assembled splittable sheath 12 and balloon 16. FIG. 5B is an end view of the assembled splittable sheath 12 and the balloon 16 received in the lumen 20. In the example shown in FIGS. 5A and 5B, the balloon 16 is positioned on the catheter body 36 of the catheter 14, and received within the lumen 20 in a folded configuration.

In some examples, the material and a thickness $T_W$ of the outer wall 30 of the sheath body 18 may be selected to provide adequate stiffness to the sheath body 18. For example, the material and the thickness $T_W$ of outer wall 30 may be selected to provide sufficient stiffness to enable the sheath body 18 to support the balloon 16 and the catheter 14 during the introduction of the balloon 16 into an introducer sheath or directly into the vasculature of a patient, such that unwanted bending and kinking of the expandable balloon 16 and the catheter 14 may be avoided. In addition, the stiffness of the sheath body 18 provided by the thickness $T_W$ of the outer wall 30 may enable the sheath body 18 to withstand, e.g., without kinking or excessive bending, the forces exerted thereupon by the expandable balloon 16 and the catheter 14 as the expandable balloon 16 is advanced through the lumen 20.

In some examples, the sheath insert 22 also contributes to the overall stiffness of the splittable sheath 12, and may help the splittable sheath 12 withstand the forces exerted thereupon as the balloon 16 is advanced through the lumen 20. In some examples, a material of the sheath insert 22 may have greater stiffness than a stiffness of a material of the sheath body 18, thereby providing a supportive spine to the splittable sheath 12, and helping to avoid kinking, excessive bending, or excessive rotation of the sheath 12 about the longitudinal axis 35. As discussed above, the extent of the overlap between the flanges 58, 60 and the outer wall 30 of the sheath body 18 may also contribute to the overall stiffness of the splittable sheath 12.

The stiffness and structural support provided to the splittable sheath 12 by the sheath insert 22 may enable selection of a more flexible material for the sheath body 18 (relative to the flexibility of the sheath insert 22) while maintaining adequate stiffness of the splittable sheath 12. In some cases, it may be advantageous for a material of the sheath body 18 to have sufficient flexibility to deform in response to an object having a dimension greater than the width $W_C$ of the channel 32 being introduced into the channel 32. For example, the flexibility of the material of the sheath body 18 may enable the width $W_C$ of the channel 32 to increase sufficiently to admit the sheath insert 22 within the channel 32 during assembly of the splittable sheath 12, or to allow the catheter body 36 to pass through the channel 32 during removal of the sheath body 18 from the catheter 14.

In the example of FIG. 5B, the outer wall 30 of the sheath body 18 is illustrated as including a single layer of material. In such examples, the single layer of material of the outer wall 30 may be any suitable material, such as, but not limited to a polymer. In other examples, the outer wall 30 may be made from a plurality of layers of materials, an outer layer being radially outward of an inner layer. In some examples, the sheath body 18 and the sheath insert 22 may be made from the same material. In other examples, the sheath insert 22 may be made from a material that is different from the sheath body 18, where the material can also be a polymer.

In examples in which the outer wall 30 is formed from multiple layers of material, the sheath body 18 may include an inner layer (not shown) disposed radially inward of an outer layer. The inner and outer layers may be formed by co-extrusion, or may be formed separately and then assembled by welding or other suitable techniques. In some examples, an inner layer of the sheath body 18 may be made at PTFE, HDPE, LDPE, or combinations thereof, and the outer layer may include a material of the amide family, such as a polyamide or a polyamide block copolymer (e.g., PEBAX or other member of the PEBA family).

In some examples, an inner layer of the sheath body 18 may have a lower coefficient of friction relative to the expandable balloon 16 of the medical device 10 than the material of the outer layer. That is, the material of an inner layer provides reduced resistance to the outer surface 48 of the expandable balloon 16 relative to the material of the outer wall 30. In some cases, it may be advantageous to reduce the sliding resistance between the expandable balloon 16 and a material of an inner surface of the sheath body 18 as the expandable balloon 16 is advanced through the lumen 20 of splittable sheath 12. For example, a sheath body material having a relatively low coefficient of friction may help preserve the integrity of a drug coating on the outer surface 48 of the expandable balloon 16, and may reduce an amount of force needed to advance the expandable balloon 16 distally through the lumen 20 of the sheath body 18 relative to a material having a higher coefficient of friction. A threshold amount of force may be needed to overcome the friction between the expandable balloon 16 and the inner surfaces of the splittable sheath 12 in the inner lumen 20. Reducing this threshold amount of force may help provide the clinician with enhanced control over the expandable balloon 16 during introduction of the expandable balloon 16 into an introducer sheath or into the vasculature of a patient.

Materials that provide a relatively low coefficient of friction relative to the outer surface 48 of the expandable balloon 16 typically are relatively flexible unless configured to be relatively thick. However, forming the entire sheath body 18 or the sheath insert 22 from a low coefficient of friction material may not impart the sheath body 18 or the sheath insert 22 with a desired structural integrity or other properties for, e.g., protecting the expandable balloon 16 from external forces during transportation and storage of the medical device 10 without making the sheath body 18 or the sheath insert 22 relatively thick. Thus, in any of the examples shown in FIGS. 1-5B, it may be desirable to provide the sheath body 18 with an outer layer that is stiffer than an inner layer having a lower coefficient of friction relative to the outer surface 48 of the expandable balloon 16, in order to provide the desired structural integrity to the splittable sheath 12 without having to be excessively thick.

The material of the outer layer of the outer wall 30 may have one or more mechanical properties (e.g., at least one of a compressive strength, a yield strength, or a tensile strength) that are stronger than the mechanical properties of the inner layer. Thus, increasing the relative thickness of the outer layer with respect to the thickness of an inner layer may provide the sheath body 18 with at least one of an increased compressive strength, a yield strength, or a tensile strength. Similarly, decreasing the relative thickness of the outer layer with respect to a thickness of an inner layer may provide the sheath body 18 with at least one of a decreased compressive strength, a yield strength, or a tensile strength. In some examples, the desired degree of overall stiffness or flexibility of the sheath body 18 may be based on any of several considerations, such as the dimensions of the expandable balloon 16 and the catheter 14.

In some examples, an inner layer of the outer wall 30 may account for about 10% to about 30% of the total thickness $T_W$ of the outer wall 30 of the sheath body 18, whereas the outer layer of the outer wall 30 may account for about 60% to about 90% of the total thickness $T_W$ of the sheath body 18. However, the relative thicknesses of an inner layer of the sheath body 18 and the outer wall 30 may vary in different examples, and may be based on a desired degree of stiffness or flexibility of the sheath body 18.

Additionally, or alternatively, the sheath insert 22 may include an inner layer and an outer layer with one or more of the characteristics described above with respect to the outer wall 30 of the sheath body 18, which may reduce an amount of force needed to advance the expandable balloon 16 distally through the lumen 20.

In other examples, the sheath body 18 and/or the sheath insert 22 may include one or more additional layers in addition to or instead of the inner and outer layers described above. For example, the sheath body 18 and/or the sheath insert 22 may include an intermediate layer between the inner and outer layers. An intermediate layer positioned between the inner and outer layers may be a bonding layer that is configured to bond the material of an inner layer of to the material of the outer layer. In some examples, an inner layer, an intermediate layer, and the outer wall 30 of the sheath body 18 and/or the sheath insert 22 may be formed separately by any suitable techniques, and then assembled by placing such an intermediate layer between the inner and outer layers, and then applying sufficient heat, pressure, or other means to bond the layers together. In other examples, an inner layer, an intermediate layer, and the outer layer may be co-extruded together, so as to form a more integral structure for the sheath body 18 and/or the sheath insert 22. In some examples, an intermediate layer may be an adhesive material, such as, but not limited to, a thermoplastic.

In examples in which the sheath body 18 includes an intermediate layer, the intermediate layer may account for about 5% to about 15% of the total thickness $T_W$ of the outer wall 30 of the sheath body 18. An inner layer and the outer wall 30 may account for the remaining 85% to 95% of the thickness $T_W$. For example, the relative thicknesses of the inner and outer layers may have a ratio of about 1:3 to about 1:6. As an example, an intermediate layer of the sheath body 18 may account for about 10% of the thickness $T_W$, an inner layer may account for about 20% of the thickness $T_W$, and the outer wall 30 may account for about 70% of the thickness $T_W$. The relative thicknesses of an inner layer and the outer wall 30 of the sheath body 18 may vary in different examples, and may be based on a desired degree of stiffness or flexibility of the sheath body 18.

Figure 6A:
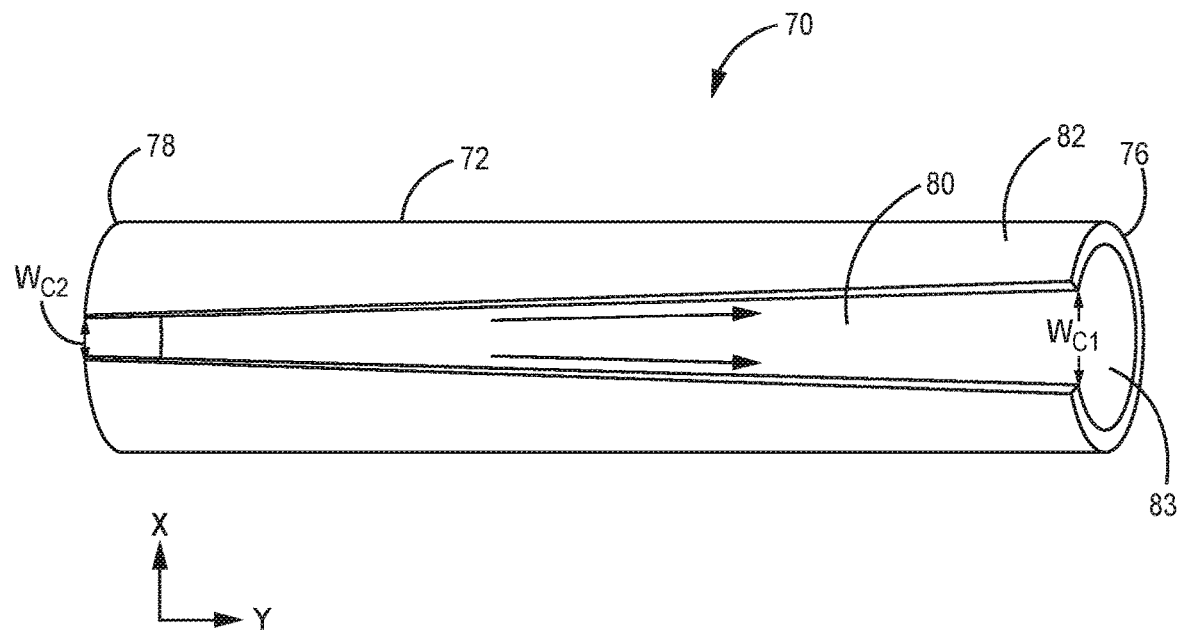
FIG. 6A is a perspective of another example sheath body of a splittable sheath, the sheath body defining a channel that increases in width towards one end of the sheath body.
Figure 6B:
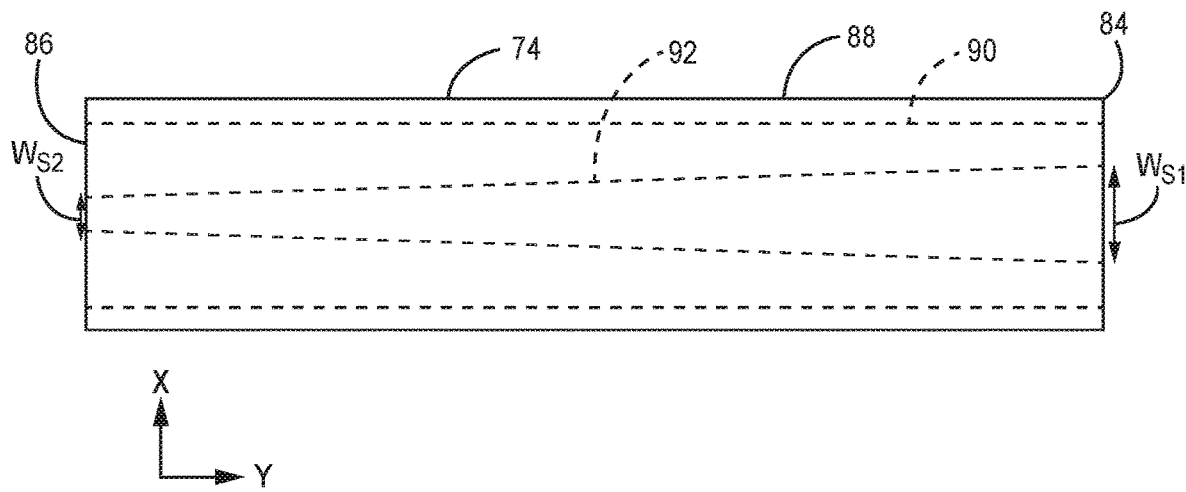
FIG. 6B is a side view of another example sheath insert that may be used with the splittable sheath of FIG. 6A, the sheath insert including a septum that is wider at one end of the sheath insert.

FIGS. 6A and 6B illustrate another example splittable sheath 70 that can be used with the medical device 10 of FIGS. 1-3. FIG. 6A is a perspective view of a sheath body 72 of the splittable sheath 70, and FIG. 6B is a top view of a sheath insert 74 of the splittable sheath 70.

In the illustrated example of FIGS. 6A and 6B, the sheath body 72 includes a proximal end 76, a distal end 78, a channel 80 configured to receive the sheath insert 74, and an outer wall 82. The splittable sheath 70 defines a lumen 83, which may be defined by the sheath body 72 when the sheath insert 74 is not received within the channel 80, or by both the sheath body 72 and the sheath insert 74 when the sheath insert 74 is received within the channel 80. The sheath insert 74 extends between a proximal end 84 and a distal end, and includes an outer flange 88, an inner flange 90, and a septum 92.

The sheath body 72 and the sheath insert 74 are similar to the sheath body 18 and the sheath insert 22 of the splittable sheath 12, but have different shapes than the sheath body 18 and the sheath insert 22 of the splittable sheath 12. For example, the splittable sheath 70 may include one or more tabs (not shown) extending from one or more ends of the sheath body 72 or the sheath insert 74. Regardless of whether the splittable sheath 70 includes one or more tabs, a clinician may split the splittable sheath 70 in any of the manners described above with respect to the splittable sheath 12.

The channel 80 defined by the sheath body 72 along a length of the channel 80 (measured in the y-axis direction, along a longitudinal axis of the sheath body 72) decreases in width from the proximal end 76 of the sheath body 72 to a distal end 78 of the sheath body 72. In the example of FIG. 6A, a channel width $W_{C1}$ at the proximal end 76 of the sheath body 72 is greater than a channel width $W_{C2}$ at the distal end 78 of the sheath body 72. In other examples, however, the wedge-shape of the channel 80 may be flip-flopped, such that the channel width $W_{C1}$ at the distal end 78 of the sheath body is less than the channel width $W_{C2}$.

The septum 92 of the sheath insert 74 has a shape corresponding to a shape of the channel 80, which allows the septum 92 to mate with the sheath body 72. In particular, the septum 92 decreases in width along a length of the sheath insert 74 (also measured along the y-axis direction) from the proximal end 84 of the sheath insert 74 to the distal end 86. The septum width $W_{S1}$ at the proximal end 84 of the septum 92 is greater than the septum width $W_{S2}$ at the distal end 86 of the septum 92. In other examples, however, the wedge-shape of the septum 92 may be flip-flopped, such that the septum width $W_{S1}$ is less than the septum width $W_{S2}$.

In some examples, one or more additional features of the sheath insert 74 may vary in width along a length of the sheath insert 74 in addition to the variable width of the septum 92. For example, the flanges 88, 90 also may vary in width in proportion with the varying width of the septum 92. In other examples, the flanges 88, 90 may have constant widths along a length of the sheath insert 74. In any such examples, the flanges 88, 90 may have widths at least as great as smallest width of the channel 80.

In contrast to the channel 80 and the septum 92 shown in FIGS. 6A and 6B, the channel 32 of the sheath body 18 shown in FIG. 4B is substantially the same width along a length of the channel (e.g., the same width but for manufacturing variances), and the septum 62 of the sheath insert 22 shown in FIG. 4B is substantially the same width along a length of the septum 62. The varying widths of the channel 80 and the septum 92 may aid the mechanical interference between the sheath body 72 and the sheath insert 74 when the sheath insert 74 is received within the channel 80, thereby contributing to the strength of a mechanical connection between the sheath body 72 and the sheath insert 74. The wedge-like shape of the channel 80 and the septum 92 shown in FIGS. 6A and 6B may help fix the relative longitudinal positions of the sheath body 72 and the sheath insert 74.

In some examples, the channel width $W_{C1}$ at the proximal end 76 of the sheath body 72 may be smaller than the septum width $W_{S1}$ at the proximal end 84 of the septum 92 of the sheath insert 74, which may increase the mechanical interference fit between the sheath body 72 and the sheath insert 74 when the sheath insert 74 is fully introduced into the channel 80 (e.g., when the distal ends of the channel 80 and the septum 92 are aligned). Additionally, or alternatively, the channel width $W_{C2}$ at the distal end 78 of the sheath body 72 may be smaller than the septum width $W_{S2}$ at the distal end 86 of the septum 92 of the sheath insert 74, which may also increase the mechanical interference fit between the sheath body 72 and the sheath insert 74 when the sheath insert 74 is fully introduced into the channel 80. Increasing the interference fit between the sheath body 72 and the sheath insert 74 in this manner may help retain the sheath insert 74 within the channel 80 when the splittable sheath 70 is in the assembled configuration.

In some examples, the channel width $W_{C1}$ may be from about 0.20 millimeters to about 2.00 millimeters and the channel width $W_{C2}$ may be from about 0.20 millimeters to about 2.00 millimeters, the first width and the second width being different values within those ranges.

In some examples, the channel width $W_{C1}$ may be from about 0.30 millimeters to about 0.75 millimeters, whereas the channel width $W_{C2}$ may be from about 0.23 millimeters to about 0.60 millimeters. The septum width $W_{S1}$ may be from about 0.40 millimeters to about 1.00 millimeters, whereas the septum width $W_{S2}$ may be from about 0.30 millimeters to about 0.75 millimeters. Thus, in such examples, the channel widths $W_{C1}$ and $W_{C2}$ may be about 60% to about 90% of the respective septum widths $W_{S1}$ and $W_{S2}$.

In examples in which relatively stronger fixation between the sheath body 72 and the sheath insert 74 is desirable, the widths $W_{C1}$ and $W_{C2}$ of the channel 80 may be relatively smaller than the widths $W_{S1}$ and $W_{S2}$ of the septum 92 compared to examples in which weaker fixation between the sheath body 72 and the sheath insert 74 is desirable. In any such examples, the materials and thicknesses of the sheath body 72 and the sheath insert 74 may be selected to provide sufficient strength to withstand the force needed to overcome the interference fit between the sheath body 72 and the sheath insert 74 when the clinician moves the sheath body 72 and/or the sheath insert 74 to separate the sheath body 72 from the sheath insert 74, which may be accomplished in a manner substantially similar to those in which the components of the splittable sheath 12 may be separated.

FIGS. 7A-9E are end views of example splittable sheaths that include sheath bodies and sheath inserts having various shapes. The splittable sheaths shown in FIGS. 7A-9E are examples of the splittable sheath 12 of FIGS. 1-5B or the splittable sheath 70 of FIGS. 6A and 6B. For example, any of the example splittable sheaths of FIGS. 7A-9E may include one or more tabs, such as the sheath body tab 24 or the sheath insert tab 34 of the splittable sheath 12. In addition, any of the example splittable sheaths of FIGS. 7A-9E may include a septum and a channel that vary in width from proximal to distal ends thereof, as described with respect to the splittable sheath 70 of FIGS. 6A and 6B.

Figure 7A:
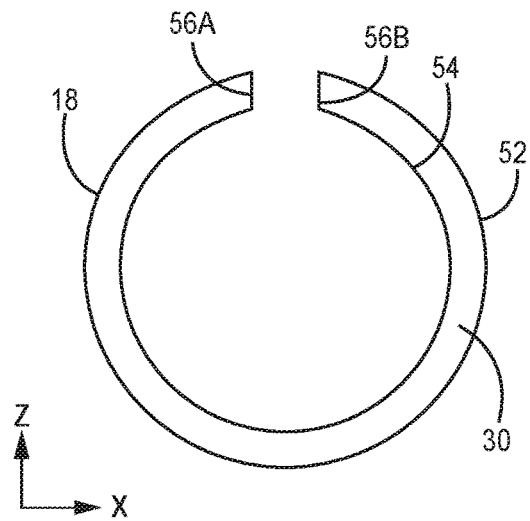
FIG. 7A is an end view of the sheath body of the splittable sheath of FIG. 1.

FIG. 7A is an end view of the sheath body 18 of the splittable sheath 12. As shown in FIG. 7A, the edges 56A, 56B of the sheath body 18 have a substantially straight shape in cross-section, such that the edges 56A, 56B are substantially parallel to each other (e.g., parallel or nearly parallel but for manufacturing variances).

Figure 7B:
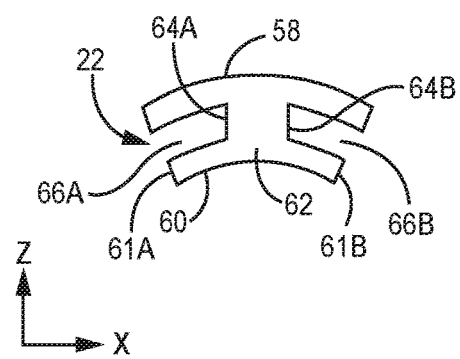
FIG. 7B is an end view of an example sheath insert usable with the splittable sheath of FIG. 1, and illustrates an example cross-sectional shape for a sheath insert.

FIG. 7B is an end view of the sheath insert 22 of the splittable sheath 12 of FIGS. 1-5B, shown in greater detail to illustrate the relationship between the edges 56A, 56B of the sheath body 18 and one or more components of the sheath insert 22. The sheath insert 22 defines a shape corresponding to the shape of the sheath insert 18 such that the sheath body 18 and the sheath insert 22 mate together. For example, in the example shown in FIGS. 7A and 7B, the first septum surface 64A and the second septum surface 64B are substantially parallel to each other. Thus, when the first edge 56A is received within the first slot 66A, the first edge 56A contacts, or is at least parallel to, with the first surface 64A of the septum 62, and when the second edge 56B is received within the second slot 66B of the sheath insert 22, the second edge 56B contacts, or is at least parallel to, the first surface 64A of the septum 62. The complementary cross-sectional shapes of the sheath body 18 and the sheath insert 22 may improve the mechanical interference fit between the sheath body 18 and the sheath insert 22 relative to examples in which there are not complementary shapes.

Figure 7C:
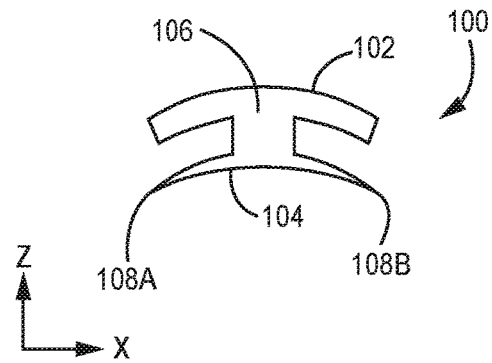
FIG. 7C is an end view of another example sheath insert usable with the splittable sheath of FIG. 1, and illustrates another example cross-sectional shape for a sheath insert.

FIG. 7C is an end view of another example sheath insert 100 usable with the sheath body 18 of the splittable sheath 12 of FIG. 1, and illustrates another example cross-sectional shape for a sheath insert. The sheath insert 100 of FIG. 7C includes an outer flange 102, an inner flange 104, and a septum 106. One or more features of the sheath insert 100 may be substantially similar to one or more corresponding features of the sheath insert 22 of FIGS. 1-5B or the sheath insert 74 of FIGS. 6A and 6B, and will not be discussed in detail again here. For example, the outer flange 102 and the septum 106 may be substantially similar to the outer flange 58 and the septum 62 of the sheath insert 22 of the splittable sheath 12.

The sheath insert 100 differs from the sheath insert 22 and the sheath insert 74 in that the inner flange 104 has tapered ends 108A, 108B instead of the blunter ends 61A, 61B of the inner flange 60 of the sheath insert 22. In some examples, the outer flange 102 may include tapered ends (not illustrated) in addition to or instead of the tapered ends of the inner flange 104. The tapered ends 108A, 108B define a relatively smooth transition between the sheath insert 100 and the sheath body 18 because the tapered ends 108A, 108B enable the inner flange 104 to maintain a relatively low profile. In this way, the tapered ends 108A, 108B may help facilitate a relatively smooth inner lumen 20 with no or few edges between the sheath both 18 and the sheath insert 100 that, for example, the balloon 16 may catch on. In addition, the lower profile inner flange 104 may help maximize the size of the lumen 20 when the splittable sheath is assembled.

Figure 7D:
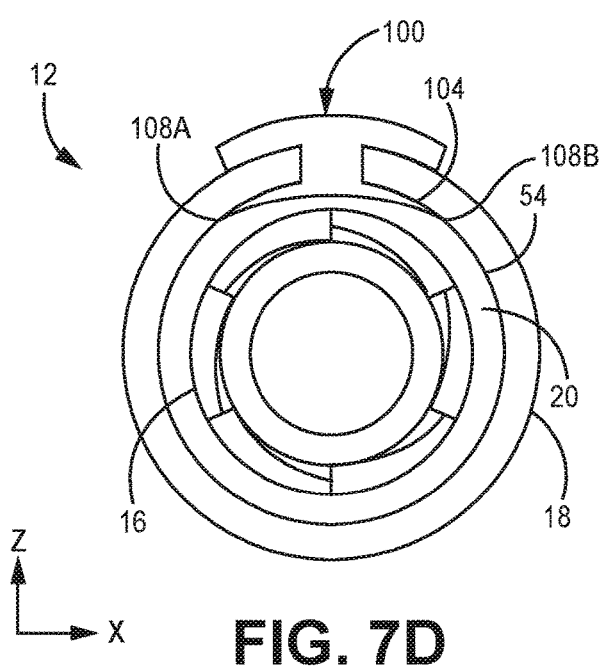
FIG. 7D is an end view of an example sheath, and illustrates the sheath insert of FIG. 7C assembled with the sheath body of FIG. 7A.

As shown in FIG. 7D, the tapered ends 108A, 108B of the inner flange 104 may enable the inner flange 104 to form a substantially continuous surface with the inner surface 54 of the outer wall 30 when the sheath insert 100 is received within the channel 32 of the sheath body 18. In some examples, the tapered ends 108A, 108B may reduce a possibility of the balloon 16 becoming snagged on or otherwise abraded by the inner flange 104 while the balloon 16 is received within the lumen 20, such as when the balloon 16 is advanced distally through the lumen 20 during a medical procedure.

Figure 8A:
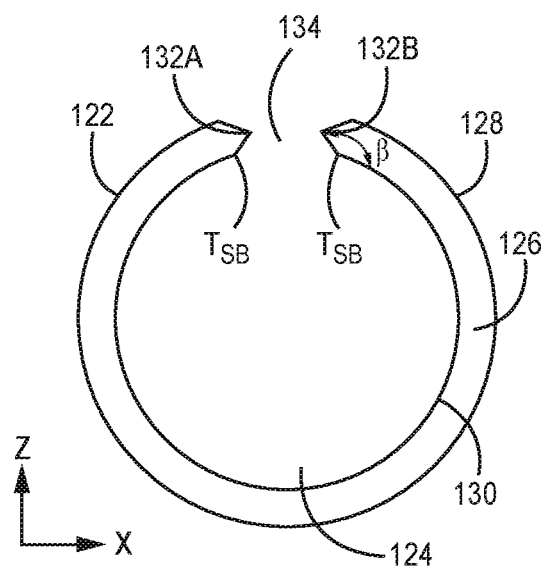
FIG. 8A is an end view of another example sheath body of a splittable sheath, the sheath body including edges defining a protrusion.

FIGS. 8A-8E are end views of one or more components of another splittable sheath 120 that may be used with the medical device 10 of FIGS. 1-3. The splittable sheath 120 defines a lumen 124 and includes a sheath body 122 (FIG. 8A) and one of the example sheath inserts illustrated in FIG. 8B, 8D, or 8E. FIG. 8A is an end view of the sheath body 122, which includes an outer wall 126 having an outer surface 128 and an inner surface 130. The outer wall 126 defines a first edge 132A, and a second edge 132B. A channel 134 is defined between the edges 132A, 132B of the outer wall 126. One or more features of the sheath body 122 may be substantially similar to one or more corresponding features of the sheath body 18 of FIGS. 1-5B or the sheath body 72 of FIGS. 6A and 6B, and will not be discussed in detail again here. The sheath body 122 may differ from the sheath body 18 or the sheath body 72 in that a pair of transition points $T_{SB}$ between the outer surface 128 and the first edge 132A and between the inner surface 130 and the second edge 132B each form an obtuse angle β of about 120 degrees to about 140 degrees, instead of the parallel edges 56A, 56B of the sheath body 18. The obtuse angle β is illustrated in FIG. 8A with respect to the second edge 132B. The cross-sectional shape of the edges 132A, 132B by the transition points $T_{SB}$ thus may be projected toward each other, defining V-shaped protrusions configured to be received in slots of a sheath insert. In other examples, other the sheath body 122 may define other shaped protrusions.

Figure 8B:
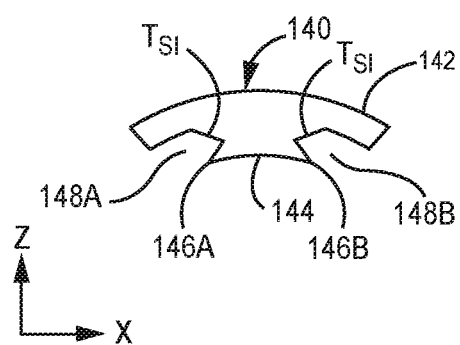
FIG. 8B is an end view of an example sheath insert usable with the splittable sheath of FIG. 8A, and illustrates a sheath insert that defines a recessed portion.

FIG. 8B is an end view of a sheath insert 140 that may be used with splittable sheath 120, and illustrates another cross-sectional shape for a sheath insert. The sheath insert 140 includes a flange 142, and a septum 144 having a first surface 146A and a second surface 146B. Unlike the sheath inserts of FIGS. 1-7D, the sheath insert 140 of FIG. 8B does not include an inner flange. Instead, the flange 142, which may be configured to be positioned on the outer surface 128 of the sheath body 122 when the sheath insert 140 is received in the channel 134, forms the sole flange of the sheath insert 140, such that the sheath insert 140 does not project into the lumen 124 when the sheath insert 140 is received in the channel 134. In some cases, a single-flange configuration of a sheath insert (e.g., sheath insert 140) may be advantageous. For example, the absence of an inner flange may enable the lumen 124 to have an inner dimension (e.g., a circumference) that is substantially equal to a corresponding inner dimension (e.g., a circumference) of the inner surface 130 of the outer wall 126, and may reduce adverse interactions of the inner surface 130 with the balloon 16.

As shown in FIG. 8B, the flange 142 and the first surface 146A of the septum 144 define a first slot 148A of the sheath insert 140, and the flange 142 and the second surface 146B of the septum 144 define a second slot 148B of the sheath insert 140. The first slot 148A and the second slot 148B of the sheath insert 140 each have cross-sectional shapes that includes a recessed portion complementary to the cross-sectional shapes of the first edge 132A and the second edge 132B, respectively, of the sheath body 122. For example, a transition point $T_{S1}$ between an inner surface of the flange 142 and the first septum surface 146A may form an angle of about 120 degrees to about 140 degrees. Due to the complementary shapes, when the first edge 132A is received within the first slot 148A and the second edge 132B is received within the second slot 148B, first and second edges 132A, 132B may be positioned in substantially continuous contact with the respective surface 146A, 146B of the septum 144.

The complementary cross-sectional shapes of the sheath body 122 and the sheath insert 140 may help retain the sheath insert 140 within the sheath body 122 until the clinician separates the sheath insert 140 from the sheath body 122. For example, the cross-sectional shapes of the edges 132A, 132B and the septum 144 may increase the area of contact between the edges 132A, 132B of the sheath body 122 and the surfaces 146A, 146B of the septum 144, relative to the example of the sheath body 18 and the sheath insert 22 of the splittable sheath 12. The increased area of contact between the sheath body 122 and the sheath insert 140 may help provide a sufficient interference fit between the sheath body 122 and the sheath insert 140 to keep the sheath body 122 and the sheath insert 140 assembled together, despite there being only a single flange 142.

Figure 8C:
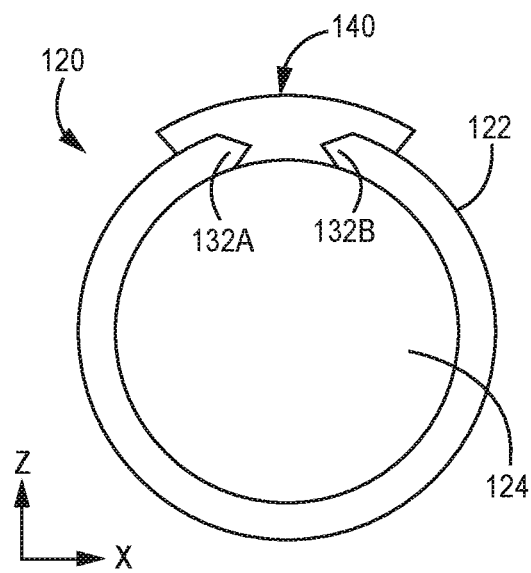
FIG. 8C is an end view of an example sheath, and illustrates the sheath insert of FIG. 8B received within the sheath body of FIG. 8A.

As shown in FIG. 8C, when the sheath body 122 and the sheath insert 140 are assembled together to define the splittable sheath 120, the lumen 124 of the splittable sheath 120 may have an inner diameter that is larger than an inner diameter of an example splittable sheath formed with the sheath body 122 and a sheath insert having both an inner flange and an outer flange. Thus, the splittable sheath 120 formed with the sheath insert 140 and the sheath body 122 may be configured to receive an expandable balloon having a larger outer dimension than splittable sheaths formed with a sheath insert having an inner flange that protrudes into a lumen of a sheath body when the sheath insert is received within the sheath body.

Figure 8D:
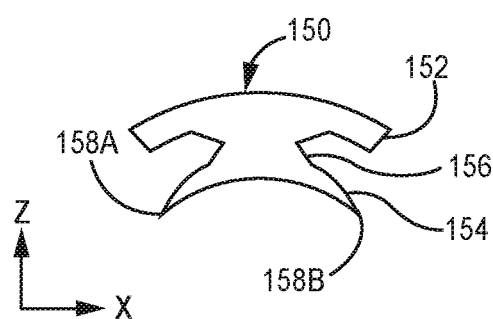
FIG. 8D is an end view of another example sheath insert usable with the splittable sheath of FIG. 8A, and illustrates another example sheath insert that defines a recessed portion.
Figure 8E:
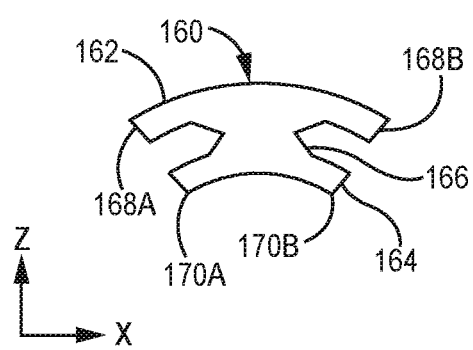
FIG. 8E is an end view of another example sheath insert usable with the splittable sheath of FIG. 8A, and illustrates another example sheath insert that defines a recessed portion.

FIGS. 8D and 8E are end views of respective sheath inserts 150 and 160 that may be used with the splittable sheath 120, and illustrate additional cross-sectional shapes for a sheath insert. In the illustrated example of FIG. 8D, the sheath insert 150 includes an outer flange 152, an inner flange 154, and a septum 156. The sheath insert 160 of FIG. 8E includes an outer flange 162, an inner flange 164, and a septum 166. One or more features of the sheath inserts 150 and 160 may be substantially similar to one or more corresponding features of the sheath insert 140 of FIG. 8B. For example, the septum 156 of the sheath insert 150 and the septum 166 of the sheath insert 160 may be substantially similar to the septum 144 of the sheath insert 140. However, the sheath inserts 150 and 160 differ from the sheath insert 140 in that the sheath inserts 150 and 160 include the respective inner flanges 154 and 164.

In addition, one or both of the outer flange 152 or the inner flange 154 of the sheath insert 150 may include tapered ends, such as tapered ends 158A, 158B of the inner flange 154 illustrated in FIG. 8C. As with previously described inserts that include tapered ends, the tapered ends 158A, 158B may provide a substantially continuous surface between the inner flange 154 of the sheath insert 160 and the inner surface 130 of the outer wall 126. In other examples, such as the example of FIG. 8E, the outer flange 162 of sheath insert 160 may include angular ends 168A, 168B, and the inner flange 164 may define ends 170A, 170B.

Figure 9A:
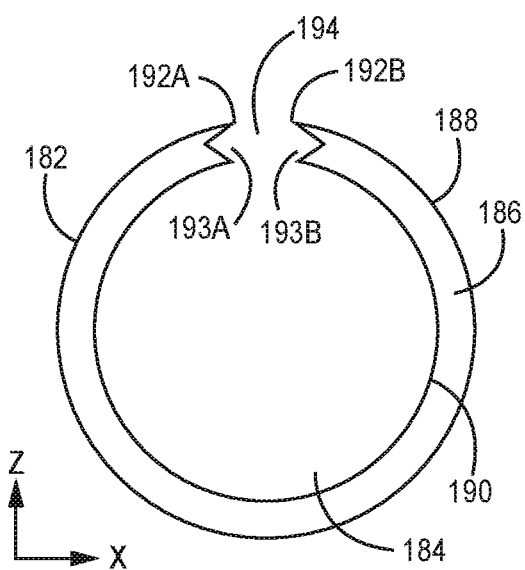
FIG. 9A is an end view of another example sheath body of a splittable sheath, the sheath body including edges defining a recess.

In the examples shown in FIGS. 8A-8E, the sheath body 122 defines a protrusion that is configured to be received in a recess defined by a sheath insert. In other examples, a sheath body may define a recess configured to receive a protrusion defined by a sheath insert, as shown in FIGS. 9A-9E. Each of FIGS. 9A-9E are end views of one or more components of another splittable sheath 180 that may be used with the medical device 10 of FIGS. 1-3. The splittable sheath 180 defines a lumen 184, and includes a sheath body 182 and one of the example sheath inserts illustrated in FIG. 9B, 9D, or 9C. FIG. 9A is an end view of the sheath body 182 of the splittable sheath 180. The sheath body 182 includes an outer wall 186 having an outer surface 188 and an inner surface 190. The outer wall 186 defines a channel 194 between a first edge 192A and a second edge 192B. One or more features of the sheath body 182 may be substantially similar to one or more corresponding features of the sheath body 18 of FIGS. 1-5B, the sheath body 72 of FIGS. 6A and 6B, or the sheath body 122 of FIGS. 8A-8D, and will not be discussed in detail again here. In some examples, the sheath body 182 differs from other example sheath bodies described herein, in that the edges 192A, 192B of the outer wall 186 define respective recesses 193A, 193B configured to receive a portion of a sheath insert in order to interlock the sheath body 182 and the sheath insert together to define the sheath 180.

Figure 9B:
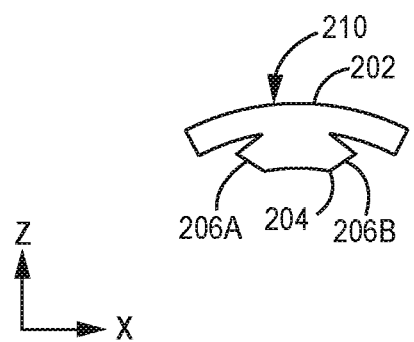
FIG. 9B is an end view of an example sheath insert usable with the splittable sheath of FIG. 9A, and illustrates an example sheath insert that defines a projected portion.
Figure 9C:
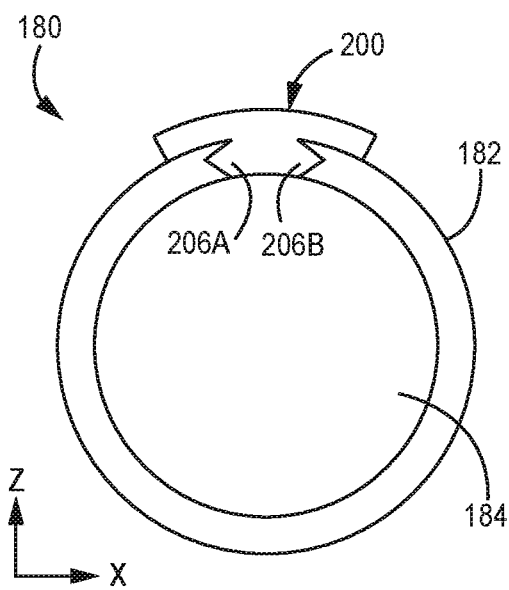
FIG. 9C is an end view of an example sheath, and illustrates the sheath insert of FIG. 9B received within the sheath body of FIG. 9A.

FIG. 9B is an end view of a sheath insert 200 that may be used with splittable sheath 180, and illustrates another cross-sectional shape for a sheath insert. In the illustrated example, the sheath insert 200 includes a flange 202, and a septum 204 defining a first protrusion 206A and a second protrusion 206B. The protrusions 206A, 206B have shapes that are complementary to the first and second recesses 193A, 193B of the sheath body 182. Thus, as shown in FIG. 9E, to assemble the splittable sheath 180, the sheath body 210 may be positioned such that protrusions 206A, 206B are introduced into respective recesses 193A, 193B of the sheath body 182.

As with the example of FIG. 8E, the lumen 184 of the splittable sheath 180 may have an inner diameter that is larger than an inner diameter of an example splittable sheath formed with the sheath body 182 and a sheath insert having both an inner flange and an outer flange, and may be configured to receive a balloon having a larger outer dimension than splittable sheaths formed with a sheath insert having an inner flange that is positioned within a lumen of the splittable sheath when the sheath insert is received within a sheath body.

Figure 9D:
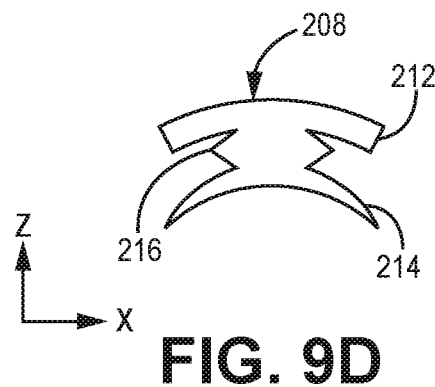
FIG. 9D is an end view of another example sheath insert usable with the splittable sheath of FIG. 9A, and illustrates another example sheath insert that defines a projected portion.
Figure 9E:
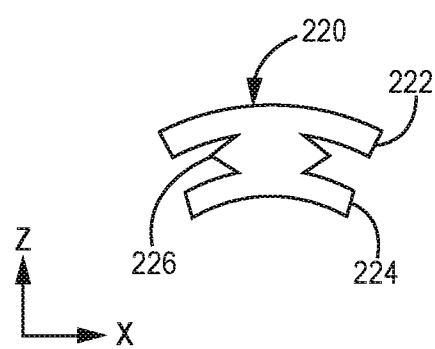
FIG. 9E is an end view of another example sheath insert usable with the splittable sheath of FIG. 9A, and illustrates another example sheath insert that defines a projected portion.

FIGS. 9D and 9E are end views of respective sheath inserts 208 and 220 that may be used with splittable sheath 180, and illustrates additional cross-sectional shapes for a sheath insert that can be configured to mate with the recesses 193A, 193B defined in the sheath body 182. In FIG. 9D, the sheath insert 208 includes an outer flange 212, an inner flange 214, and a septum 216. The sheath insert 220 of FIG. 9E includes an outer flange 222, an inner flange 224, and a septum 226. One or more features of the sheath inserts 208 and 220 may be substantially similar to one or more corresponding features of the sheath inserts 150 and 160 of FIGS. 8D and 8E, although the septa 216, 226 of the corresponding sheath inserts 208, 220 may define projections, instead of the recessed cross-sectional shape of the septa 156, 166 of the sheath inserts 160, 166. In some examples, one or more additional features or advantages of the cross-sectional shapes of the sheath inserts 208, 220 may be substantially similar to those described with respect to the respective sheath inserts 150, 160 of FIGS. 8D and 8E.

The various example cross-sectional shapes of the sheath inserts and the edges of the sheath bodies of the example splittable sheaths described above with respect to FIGS. 7A-9E is intended to be illustrative and not exhaustive. For example, the example cross-sectional shapes of the example sheath described herein may be modified, such as by eliminating an illustrated upper flange or lower flange, by combining two or more of the shapes illustrated herein, by modifying a dimension of any portion of a shape of a sheath insert (e.g., a shape of a septum, an upper flange, or a lower flange) relative to another portion of the shape of the sheath insert, and the like. The cross-sectional shapes of the edges of the example sheath bodies above with respect to FIGS. 7A-9E may be varied in a similar manner, and various additional combinations of sheath inserts and sheath bodies are possible.

In some examples, a cross-sectional shape of one or both of a sheath insert and a sheath body of a splittable sheath may be selected based on a desired amount of physical contact (and thus, friction) between the outer edges of the sheath body and the components of the sheath insert, a desired amount of radial interference between a balloon and an inner surface of a splittable sheath, or the cost of manufacturing a particular shape, although other considerations also may affect a choice of the cross-sectional shapes of the sheath inserts and the edges of the sheath bodies. In all examples described herein, the cross-sectional shapes of the sheath inserts and the cross-sectional shapes of the edges of the sheath bodies may provide splittability along a predetermined path and into predetermined portions, relative to example sheaths that include a sheath body having an uninterrupted cross-sectional shape.

Figure 10A:
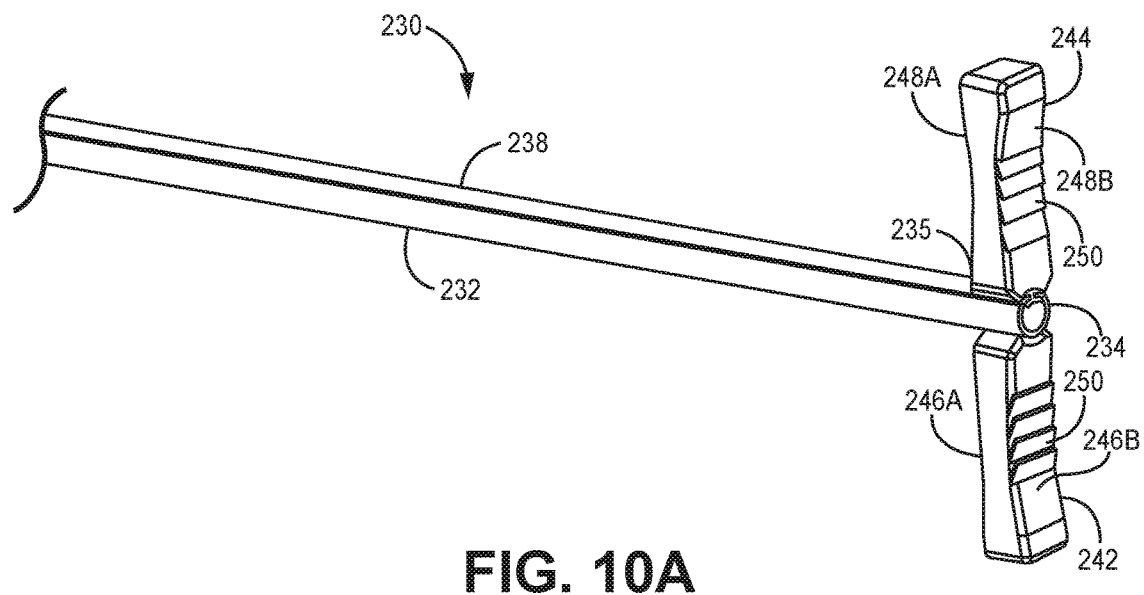
FIG. 10A is a perspective view of another example splittable including a sheath body tab and a sheath insert tab.
Figure 10B:
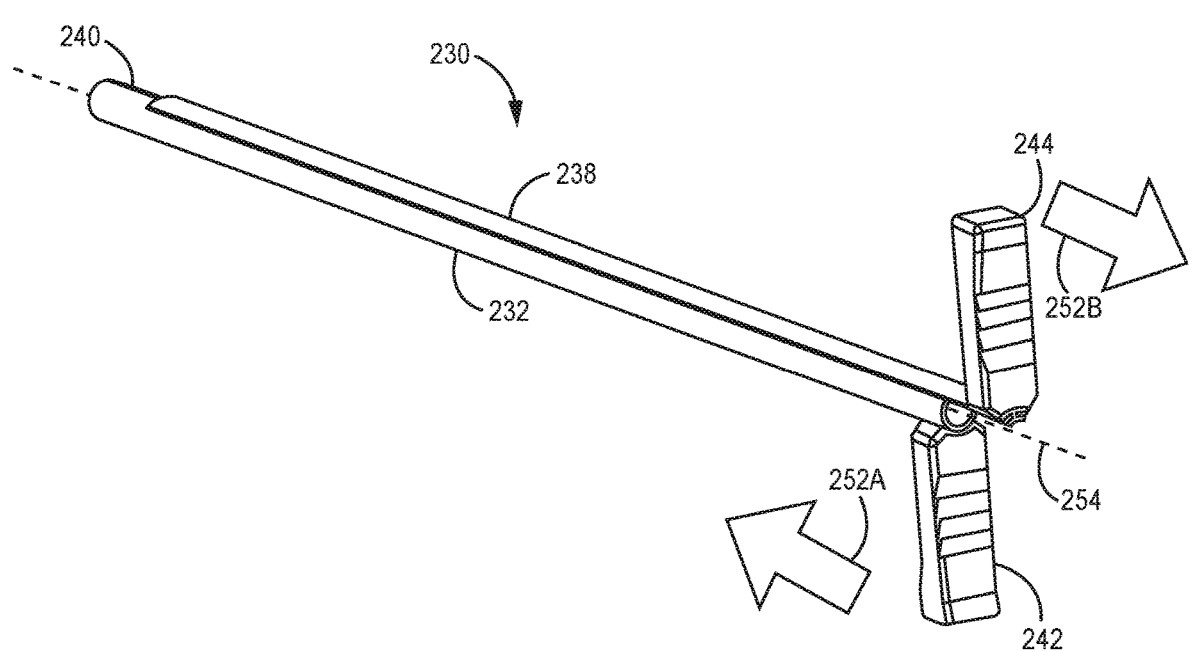
FIG. 10B is a perspective view of the splittable sheath of FIG. 10A, and illustrates directions in which the sheath body tab and the sheath insert tab are movable to separate the sheath body and the sheath insert.

FIGS. 10A and 10B illustrate another example splittable sheath 230 that may be used with the medical device 10 of FIGS. 1-3, and another example direction in which components of a splittable sheath may be moved in order to separate a sheath insert from a sheath body. The splittable sheath 230 includes a sheath body 232 and a sheath insert 238. FIG. 10A is a perspective view of the splittable sheath 230, with the sheath insert 238 received in a channel 240 defined by the sheath body 232 (shown in FIG. 10B) to form the assembled configuration of the splittable sheath 230 shown in FIG. 10A. The sheath body 232 includes a sheath body tab 242 that extends from a proximal end 234 of the sheath body 232, and the sheath insert 238 includes a sheath insert tab 244 that extends from a proximal end 235 of the sheath insert 238.

One or more features of the splittable sheath 230 of FIGS. 10A and 10B may be substantially similar to the corresponding features of the splittable sheaths 12 and 70 described above with respect to FIGS. 1-6B, and will not be discussed again in detail here. For example, the sheath body 232 and the sheath insert 238 may be substantially similar to the sheath bodies 12 and 72 or the sheath inserts 22 and 100 of FIGS. 1-6B. The splittable sheath 230 differs from the splittable sheaths 12 and 70 shown in FIGS. 1-6B in that the tabs 242, 244 are not formed integrally with the sheath body 232 and the sheath insert 238, but instead are separately formed from the sheath body 232 and the sheath insert 238, and attached to respective ones of the sheath body 232 and the sheath insert 238 by any suitable mechanical mechanism. Further, the tabs 242, 244 extend from the splittable sheath 230 in a different direction than the tabs of the splittable sheaths 12 and 70. In particular, the tabs 242, 244 extend away from the sheath body 232 and the sheath insert 238, respectively, in a direction orthogonal to the longitudinal axis of the splittable sheath 230. In some examples, the tabs 242, 244 extending in this direction may be easier to grasp by a clinician when applying a pulling force to the sheath body 232 and/or the sheath insert 238 in a direction parallel to the longitudinal axis compared to the tabs 24, 34 of the splittable sheath (FIGS. 4A and 4B).

In addition, the tabs 242, 244 of the splittable sheath 230 may vary from the tabs 24, 34 of the splittable sheath 12, in that the tabs 242, 244 include additional gripping surfaces. The sheath body tab 242 may include major surfaces 246A and 246B on opposite sides of the sheath body tab 242, and the sheath insert tab 244 may include major surfaces 248A and 248B on opposite sides of the sheath insert tab 244. In the illustrated example of FIGS. 10A and 10B, the tabs 242, 244 may include one or more ridges 250 along one or more of the major surfaces 246A, 246B and 248A, 248B of the respective tabs 242, 244. In some examples, the ridges 250 provide a gripping surface for a clinician's hands or tools, thereby enabling the clinician to obtain a secure hold on the tabs 242, 244 during a medical procedure involving the splittable sheath 230 and enhancing the efficiency of a medical procedure involving the splittable sheath 230. In other examples, in addition to or instead of the ridges 250, gripping surfaces may be provided in the tabs 242, 244 in the form of one or more holes or recesses in the major surfaces 246A, 246B and 248A, 248B of the respective tabs 242, 244. Such gripping surfaces also may help the clinician's finger or tool from slipping away from the tabs 242, 244, by providing an alternate form of gripping surface.

FIG. 10B is a perspective view of the splittable sheath 12 of FIG. 10A, which illustrates the sheath body tab 242 and the sheath insert tab 244 being moved longitudinally apart in opposite directions 252A, 252B. When a clinician moves tab 242 in the direction 252A and/or tab 244 in the directions 252B, the sheath insert 238 may be slid longitudinally out from the channel 240 of the sheath body 232 in a proximal direction, rather than pulled radially outward through the channel 240. In other examples, however, the sheath insert 238 may be separated from the sheath body 232 by pulling the sheath body tab 242 and/or the sheath insert tab 244 outward away from the longitudinal axis 254 of the sheath 230. A clinician may choose to separate the sheath insert 238 from the sheath body 232 in one manner over another based on, for example, the presence of any physical obstacles present within a space surrounding the splittable sheath 230 during a medical procedure, or based the orientation of the tabs 242, 244 about the longitudinal axis 254.

Figure 11:
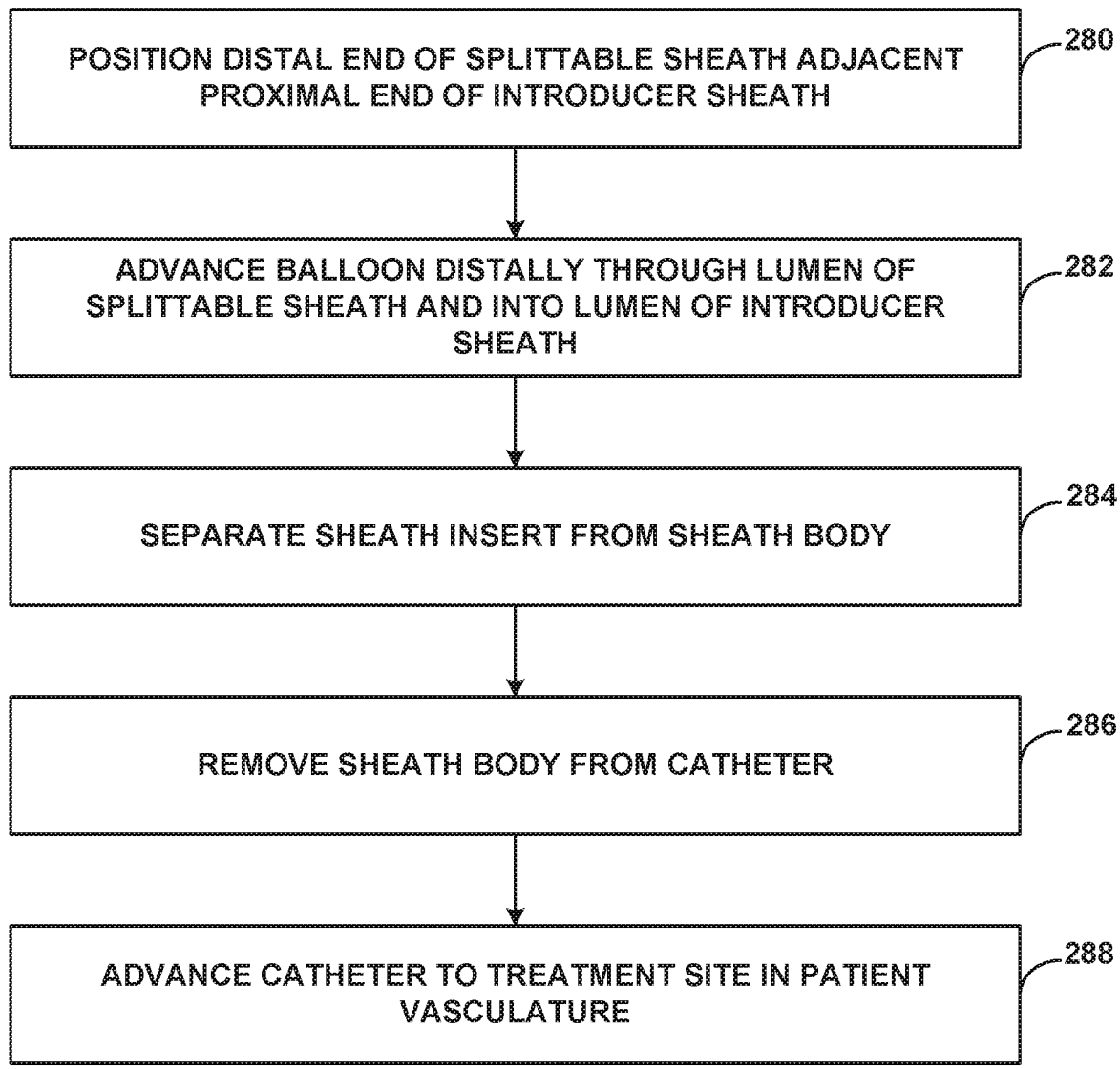
FIG. 11 is a flow diagram illustrating an example method of using a medical device as described herein.

FIG. 11 is a flow diagram illustrating an example technique that may be implemented by a clinician to deploy and use a medical device, such as the medical device 10, within the vasculature of a patient as described herein. The flow diagram of FIG. 11 is described in conjunction with FIGS. 12A-12E, which illustrate a series of side views showing the expandable balloon 16 of the medical device 10 of FIG. 1 being advanced through the splittable sheath 12 and into a vessel 260 of a patient 262, as well as the splitting and removal of the splittable sheath 12 from the catheter 14. While FIG. 11 is described in context with the splittable sheath 12 of FIGS. 1-5B, the techniques of FIG. 11 may be used in conjunction with other techniques or other splittable sheaths (e.g., the splittable sheaths of FIGS. 6A-10B). In addition, in the example of FIGS. 12A-12E, an introducer sheath 266 is illustrated as being inserted through the skin 264 of the patient 262 and into the vessel 260. In some examples, the introducer sheath 266 may be inserted through skin 264 of the patient 262 and into the vessel 260 prior to positioning the distal end 26 of the splittable sheath 12 adjacent the proximal end 268 of the introducer sheath 266. In other examples, the introducer sheath 266 may not be used in the technique illustrated in FIGS. 11-12E, or an introducer sheath having a different configuration than the introducer sheath 266 may be used.

Figure 12A:
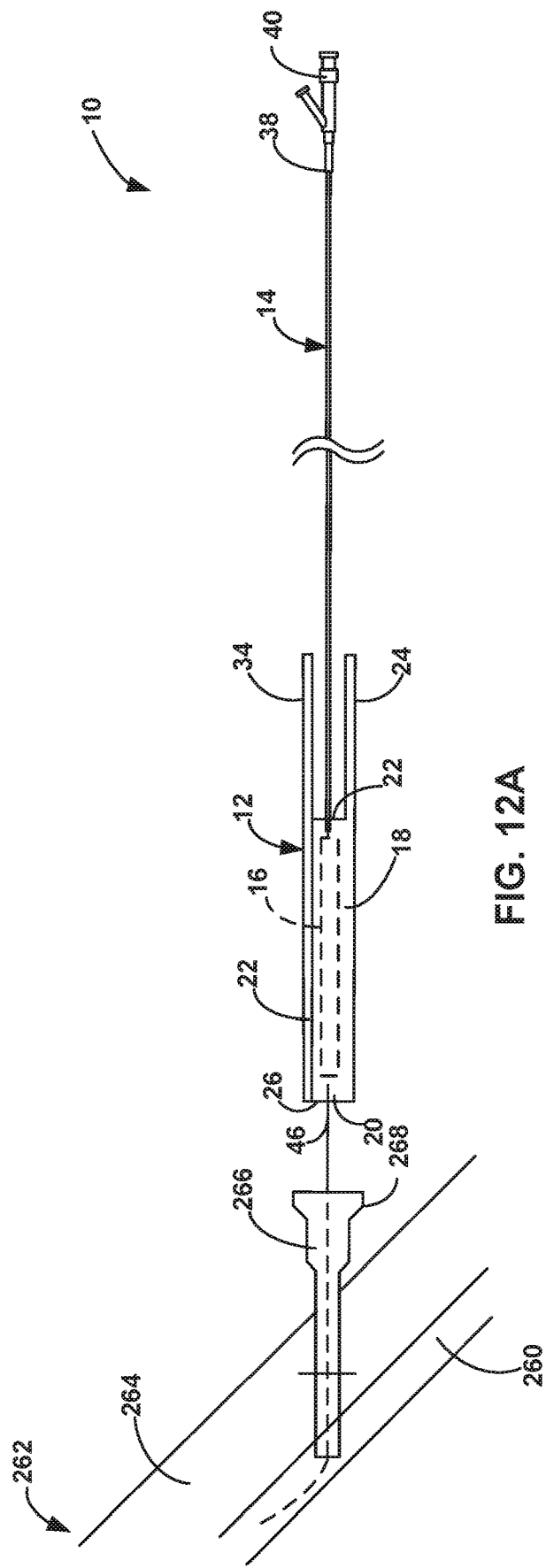
FIGS. 12A-12E are a series of side views showing an example medical device being operated in accordance with the techniques described with respect to the example method of FIG. 11.

As shown in FIG. 12A, the distal end 26 of the splittable sheath 12 may be advanced over the guidewire 46, which may extend distally from the distal end 26 of the splittable sheath 12, through the introducer sheath 266, and into the vessel 260. In the illustrated example, the guidewire 46 also extends proximally from the distal end 26 of the splittable sheath 12, into the lumen 20, and through the catheter 14 on which the expandable balloon 16 is positioned. The guidewire 46 may extend further proximally through a portion of the catheter 14 that extends proximally of the tabs 24, 34 of the splittable sheath 12 and into the hub 40, from which a clinician may manipulate the guidewire 46 as needed.

Figure 12B:
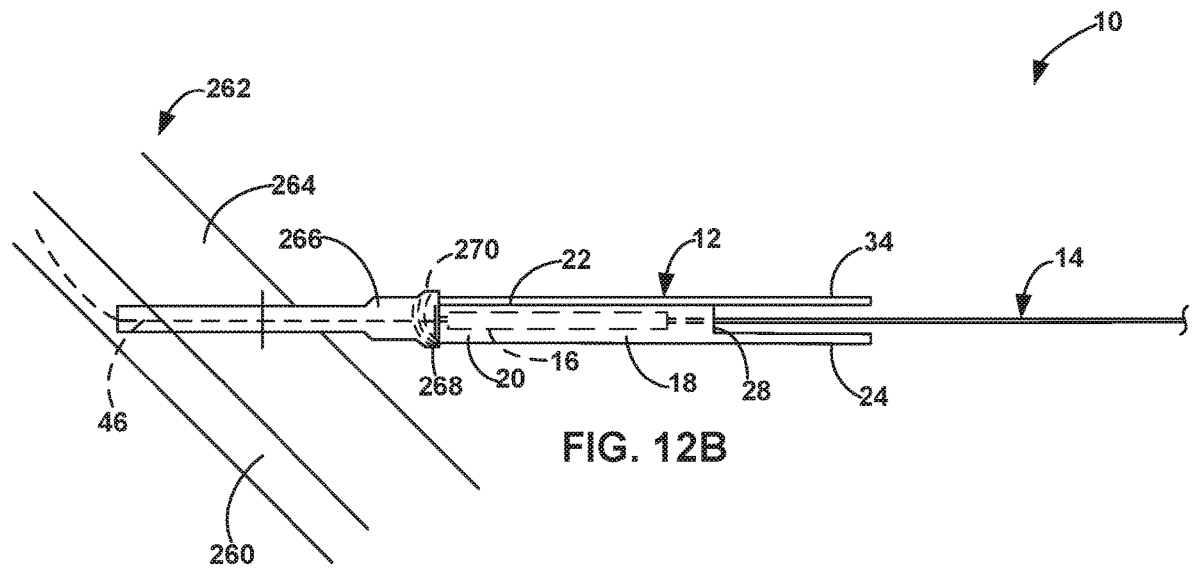

The technique of FIG. 11 includes positioning the distal end 26 of the splittable sheath 12 adjacent the proximal end 268 of the introducer sheath 266 (280), as shown in FIG. 12B. In some examples, the distal end 26 of the splittable sheath 12 may be configured to be securely received within the proximal end 268 of the introducer sheath 266, such as by a mating connection therebetween. In some such examples, the distal end 26 of the splittable sheath 12 may be stably received by the introducer sheath 266 to enable a smooth transfer of the expandable balloon 16 from the lumen 20 of the splittable sheath 12 to the introducer sheath 266. For example, the distal end 26 of the splittable sheath 12 may function as a male Luer adapter that engages a feature of the introducer sheath 266 that may function as a female Luer adapter, and one or more threads or projections 270 positioned on an internal surface of the introducer sheath 266. The threads or projections 270 of the introducer sheath 266 may be configured to mechanically engage with the distal end 26 of the splittable sheath 12 and separably retain the distal end 26 of the sheath body within the introducer sheath 266. In other examples, the distal end 26 of the splittable sheath 12 may engage the introducer sheath 266 by being received within a lumen 272 of the introducer sheath 266 in a simple mating connection.

Figure 12C:
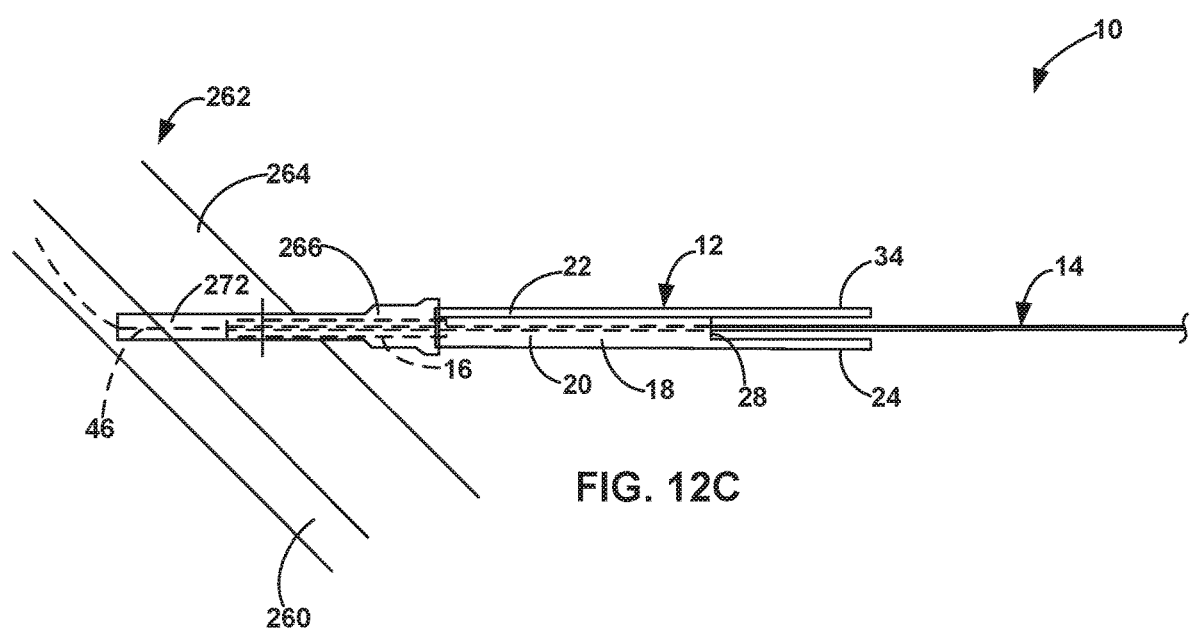

As illustrated in FIG. 12C, the clinician advances the expandable balloon 16 distally through the lumen 20 of the splittable sheath 12 and into the lumen 272 of the introducer sheath 266 (282). In some examples, the clinician may advance the expandable balloon 16 distally into the lumen 272 of the introducer sheath 266 by applying a distally-directed force to a portion of the catheter 14 that extends proximally of the splittable sheath 12 or to the hub 40 (shown in FIG. 12A). In some such examples, the clinician may advance the expandable balloon 16 and catheter 14 over the guidewire 46 into the introducer sheath 266 while the splittable sheath 12 remains substantially stationary relative to the introducer sheath 266 while the catheter 14 and the expandable balloon 16 move relative to the splittable sheath 12, as depicted by the relative positioning of the splittable sheath 12 and the expandable balloon 16 in FIG. 12B and FIG. 12C. Thus, the clinician may advance the expandable balloon 16 through the lumen 20 of the splittable sheath 12, through the lumen 272 of the introducer sheath 266 and into the vessel 260 of the patient 262 without manually handling the balloon 16 or otherwise exposing the outer surface 48 of the expandable balloon 16 to the external environment. As discussed above, minimizing directly physical contact with the expandable balloon 16 may help avoid loss of drug coating, kinking, stretching, self-adhesion of balloon components, or inadvertent removal of a coating on an outer surface of the balloon 16 that may occur during handling if the expandable balloon 16 is not protected.

Figure 12D:
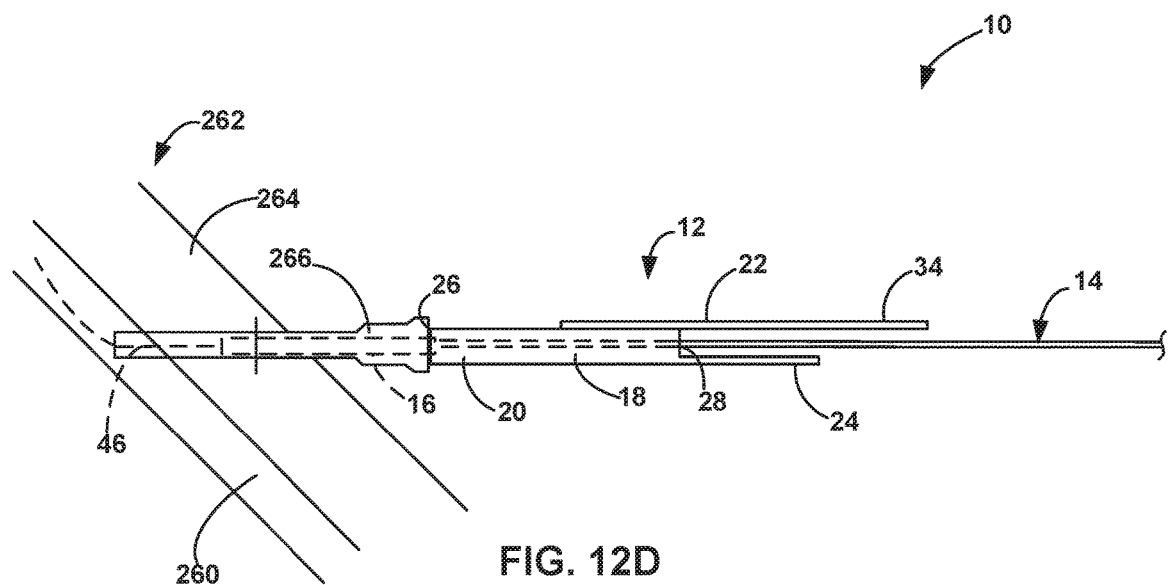

Once the expandable balloon 16 has been advanced through the lumen 20 of the splittable sheath 12 and into the introducer sheath 266, the clinician may separate the sheath insert 22 from the sheath body 18 using any of the techniques described above. For example, the clinician may grasp the sheath body tab 24 and the sheath insert tab 34, and move the sheath insert tab 34 proximally while holding the sheath body tab 24 substantially stationary to separate the sheath body 18 and the sheath insert 22 (284). In this example, the splittable sheath 12 may split in a distal-to-proximal direction as the sheath body 18 and the sheath insert 22 are moved relative to one another (e.g., such that the channel 32 is exposed in the distal-to-proximal direction), as illustrated in the example of FIG. 12D.

As described above, the movability of the sheath body 18 and the sheath insert 22 relative to one another along the edges 56A, 56B of the sheath body 18 provides a predictable path along which the clinician may readily split the splittable sheath 12 once the expandable balloon 16 has been advanced through the lumen 20 and into the introducer sheath 266. The threshold amount of splitting force needed to separate the sheath body 18 and the sheath insert 22 may be sufficient to retain the sheath insert 22 within the channel 32 of the sheath body 18 during transport and use of the splittable sheath 12, while being low enough to help a clinician retain control over the splittable sheath 12 during the separation of the sheath body 18 and the insert 22. Enhancement of the clinician's control over the splittable sheath 12 during the technique of FIG. 11 helps avoid a sudden splitting of the splittable sheath 12 and an unintended transfer of force to other portions of a medical device, which may dislodge the introducer sheath 266 or the guidewire 46 from the vessel 260.

Figure 12E:
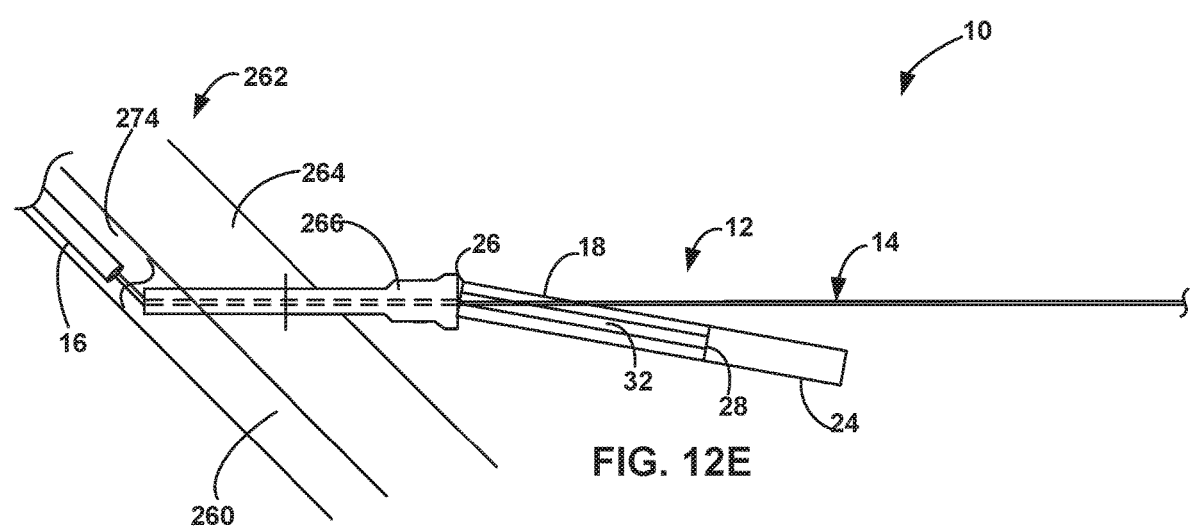

After the sheath insert 22 is fully removed from the channel 32 of the sheath body 18, the splittable sheath 12 is split into two separate portions 18, 22. In the example illustrated in FIG. 12E, the sheath insert 22 has been removed from the channel 32 such that only the sheath body 18 remains positioned over the catheter 14. With the sheath insert 22 fully removed from the channel 32, the sheath body 18 then may be removed from over the catheter 14 by passing the catheter body 36 through the channel 32 (286). The side view of FIG. 12E shows the sheath body 18 rotated approximately 90° about the central longitudinal axis 35 of the splittable sheath 12 from the view shown in FIG. 12D, to illustrate the catheter body 36 passing through the channel 32. With the splittable sheath 12 removed from the catheter 14, the clinician then may advance the expandable balloon 16 through the vessel 260 to the treatment site 274, as also shown in FIG. 12E (288). In some examples, the treatment site 274 may be located in a portion of the vessel 260. In other examples, the treatment site 274 may be located within a vessel that branches off from the vessel 260.

Removing the splittable sheath 12 from the catheter 14 enables the clinician to advance substantially all of the usable length of the catheter 14 into the vasculature of the patient 262 if needed, thereby enabling the expandable balloon 16 to be delivered to more distal treatment sites than example medical devices in which a balloon sheath is not removable from a catheter on which a balloon or other intravascular medical devices is positioned. Once the expandable balloon 16 is positioned at the treatment site 274, the clinician then may introduce a fluid into the expandable balloon 16 to inflate the same and continue performing the medical procedure, which may include placing a stent or delivering drug at the treatment site 274.

Various aspects of the disclosure have been described. These and other aspects are within the scope of the following claims.

What is claimed is:

1. A device comprising:
   a sheath body including a wall defining a lumen configured to receive an expandable balloon of a catheter, the wall defining a channel extending longitudinally at least partially between a proximal end of the sheath body and a distal end of the sheath body; and
   a sheath insert configured to close the channel, the sheath insert comprising:
      a septum configured to be removably received within the channel; and
      a flange configured to retain the septum within the channel when the septum is received within the channel, wherein the flange is radially inward from a bottom of the septum or radially outward from a top of the septum when the septum is received within the channel.

2. The device of claim 1, wherein the sheath insert is configured to extend at least partially between the proximal end of the sheath body and the distal end of the sheath body when the septum is received within the channel.

3. The device of claim 2, wherein the sheath insert is configured to extend from the proximal end of the sheath body to the distal end of the sheath body when the septum is received within the channel.

4. The device of claim 1, wherein the sheath insert and the sheath body are movable relative to each other in only a longitudinal direction when the septum is received within the channel.

5. The device of claim 1, wherein the sheath insert is configured to retain the sheath body in a substantially tubular shape.

6. The device of claim 1, wherein the flange is an outer flange and the sheath insert further includes an inner flange extending from the septum and configured to be received within the lumen of the sheath body when the septum is received within the channel.

7. The device of claim 6, wherein the sheath body defines an inner surface facing the lumen and an outer surface, and wherein the outer flange is configured to contact the outer surface of the wall of the sheath body when the septum is received within the channel, and the inner flange is configured to contact the inner surface of the wall of the sheath body when the septum is received within the channel.

8. The device of claim 1, where a shape of a cross-section of the sheath insert taken orthogonal to a longitudinal axis of the sheath insert is one of an I-shape or a T-shape.

9. The device of claim 1, wherein the flange is configured to extend along an outer surface of the wall of the sheath body when the septum is received within the channel.

10. The device of claim 1, wherein the wall of the sheath body defines a recess, and wherein the flange is configured to be received within the recess when the septum is received within the channel.

11. The device of claim 10, wherein a thickness of the flange is substantially equal to a depth of the recess such that an outer surface of the flange is flush with an outer surface of the wall of the sheath body when the septum is received within the channel.

12. The device of claim 1, wherein the wall of the sheath body defines:
   a first edge extending longitudinally at least partially between the proximal end of the sheath body and the distal end of the sheath body; and
   a second edge extending longitudinally at least partially between the proximal end of the sheath body and the distal end of the sheath body, wherein the first edge and the second edge are separated by the channel.

13. The device of claim 12, wherein a first distance between the first edge and the second edge at a proximal portion of the sheath body is different from a second distance between the first edge and the second edge at a distal portion of the sheath body.

14. The device of claim 12, wherein a distance between the first and second edges is substantially constant along a length of the first edge, the distance being measured in a direction orthogonal to a longitudinal axis of the sheath insert.

15. The device of claim 12, wherein the first edge of the sheath body is configured to contact a first surface of the septum and the second edge of the sheath body is configured to contact a second surface of the septum when the septum is received within the channel, the first surface and the second surface of the septum extending longitudinally along opposite sides of the septum.

16. The device of claim 15, wherein less than an entirety of the first edge of the sheath body is configured to contact the first surface of the septum, and wherein less than an entirety of the second edge of the sheath body is configured to contact the second surface of the septum when the septum is received within the channel.

17. The device of claim 15, wherein at least one of the first surface of the septum or the second surface of the septum includes a lubricious coating.

18. The device of claim 1, wherein the septum is configured to be held within the channel by a mechanical interference fit.

19. The device of claim 1, wherein the sheath insert includes a tab extending from one of a proximal end or a distal end of the sheath insert, the tab defining a user gripping surface, and wherein, when the septum is received within the channel, the sheath insert and the sheath body are configured to be separated from each other in response to a pulling force applied to the tab of the sheath insert in a direction away from the sheath body.

20. The device of claim 19, wherein the tab comprises a first tab, the sheath body including a second tab extending from the one of the proximal end or the distal end of the sheath insert, and wherein the sheath insert and the sheath body are configured to be separated from each other in response to movement of at least one of the first tab of the sheath insert or the second tab of the sheath body in a direction away from a central longitudinal axis of the sheath.

21. A device comprising:
   a catheter comprising:
      a catheter body; and
      an expandable balloon positioned on the catheter body; and
   a sheath comprising:
      a sheath body including a wall defining a lumen configured to receive the expandable balloon, the wall defining a channel extending longitudinally at least partially between a proximal end of the sheath body and a distal end of the sheath body; and
      a sheath insert configured to close the channel, the sheath insert comprising:
         a septum configured to be removably received within the channel; and
         a flange extending from the septum and configured to retain the septum within the channel when the septum is received within the channel, wherein the flange is radially inward from a bottom of the septum or radially outward from a top of the septum when the septum is received within the channel.

22. The device of claim 21, wherein the sheath body defines an inner surface facing the lumen, the device further comprising a pharmacologically-active agent on an outer surface of the balloon, wherein a material of the inner surface of the sheath body is substantially chemically non-reactive with the pharmacologically-active agent.

23. The device of claim 21, wherein sheath body defines an inner surface facing the lumen, and wherein, when the expandable balloon is received within the lumen of the sheath body and the septum is received within the channel, the expandable balloon is configured to exert a radially-outward force on the inner surface of the sheath body.

24. A method comprising:
   separating a sheath from a catheter, wherein separating the sheath from the catheter comprises separating a sheath body of the sheath and a sheath insert of the sheath, the sheath being disposed around an expandable balloon of the catheter, the sheath comprising:
      a sheath body including a wall defining a lumen configured to receive the expandable balloon, the wall defining an inner surface facing the lumen, an outer surface, and a channel between the inner surface and the outer surface that extends longitudinally at least partially between a proximal end of the sheath body and a distal end of the sheath body; and
      the sheath insert, the sheath insert comprising:
         a septum configured to be removably received within the channel; and
         a flange configured to retain the septum within the channel when the septum is received within the channel, wherein the flange is radially inward from a bottom of the septum or radially outward from a top of the septum when the septum is received within the channel.

25. The method of claim 24, further comprising, before separating the sheath body and the sheath insert, advancing the expandable balloon distally through the lumen of the sheath body and into a lumen of an introducer.

* * * * *